United States Patent
Brooks et al.

(10) Patent No.: US 9,943,566 B2
(45) Date of Patent: Apr. 17, 2018

(54) NF-κB INHIBITOR COMPOSITION FOR SKIN HEALTH

(71) Applicant: Geoffrey Brooks Consultants, LLC, Reno, NV (US)

(72) Inventors: Geoffrey J. Brooks, Reno, NV (US); Rajendra S. Bhatnagar, Burlingame, CA (US); Andrew P. Banham, Jacksonville, FL (US)

(73) Assignee: Geoffrey Brooks Consultants, LLC, Reno, NV (US)

( * ) Notice: Subject to any disclaimer, the term of this patent is extended or adjusted under 35 U.S.C. 154(b) by 0 days.

(21) Appl. No.: 15/461,320

(22) Filed: Mar. 16, 2017

(65) Prior Publication Data
US 2017/0266258 A1 Sep. 21, 2017

Related U.S. Application Data

(60) Provisional application No. 62/309,010, filed on Mar. 16, 2016.

(51) Int. Cl.
| | |
|---|---|
| *C07K 5/10* | (2006.01) |
| *C07K 7/06* | (2006.01) |
| *A61Q 19/00* | (2006.01) |
| *A61Q 19/08* | (2006.01) |
| *A61K 38/00* | (2006.01) |
| *A61K 38/18* | (2006.01) |
| *A61K 8/64* | (2006.01) |
| *A61K 38/08* | (2006.01) |
| *A61K 9/00* | (2006.01) |

(52) U.S. Cl.
CPC .......... *A61K 38/1841* (2013.01); *A61K 8/64* (2013.01); *A61K 9/0014* (2013.01); *A61K 38/08* (2013.01); *A61Q 19/08* (2013.01)

(58) Field of Classification Search
CPC ........ A61K 38/00; A61Q 19/00; A61Q 19/08; C07K 5/0806; C07K 5/10; C07K 7/06
USPC .......................................... 530/300, 329, 327
See application file for complete search history.

(56) References Cited

U.S. PATENT DOCUMENTS

| | | | | |
|---|---|---|---|---|
| 5,661,127 A | * | 8/1997 | Bhatnagar | A61L 27/227 424/484 |
| 5,837,224 A | | 11/1998 | Voorhees et al. | |
| 7,368,430 B2 | | 5/2008 | Aggarwal et al. | |
| 7,553,929 B2 | | 6/2009 | Hawiger et al. | |
| 2002/0010134 A1 | * | 1/2002 | Bhatnagar | A61L 27/227 514/8.9 |
| 2004/0123343 A1 | * | 6/2004 | La Rosa | C07K 14/415 800/278 |
| 2009/0075902 A1 | | 3/2009 | Robbins et al. | |
| 2011/0245182 A1 | | 10/2011 | Perricone | |
| 2011/0245183 A1 | | 10/2011 | Perricone | |
| 2015/0099692 A1 | | 4/2015 | Kim et al. | |
| 2015/0252073 A1 | | 9/2015 | Hahn et al. | |
| 2017/0051012 A1 | | 2/2017 | Bhatnagar | |

OTHER PUBLICATIONS

UniProt A0A0V1DKM5, pp. 1-2. Integrated into UniProtKB/TrEMBL on Mar. 16, 2016.*
UniProt A0A0J7Y2B7, pp. 1-3. Integrated into UniProtKB/TrEMBL on Oct. 14, 2015.*

* cited by examiner

*Primary Examiner* — Julie Ha
(74) *Attorney, Agent, or Firm* — Wolf Patent Services LLC

(57) ABSTRACT

A novel NF-κB-inhibitor peptide is a component in a skin care composition comprising the NF-κB-inhibitor and a dermatologically acceptable carrier. The composition may also include at least one additional skin care active. Additionally, the composition may include a peptide that acts as a TGF-β1 mimic. Means for treating mature, languished skin with compositions comprising the peptide are also provided.

15 Claims, No Drawings

NF-κB INHIBITOR COMPOSITION FOR SKIN HEALTH

CROSS-REFERENCES TO RELATED APPLICATIONS

This application claims the benefit of U.S. Provisional Application No. 62/309,010, filed 16 Mar. 2016. The entire contents of that application are hereby incorporated by reference herein.

BRIEF DESCRIPTION OF THE INVENTION

The present invention relates to a skin care composition containing the NF-κB-inhibitor peptide, N-M-A-N-A-K (SEQ ID NO: 1). In accordance with one embodiment, a composition comprises N-M-A-N-A-K (SEQ ID NO: 1) and a dermatologically suitable carrier. In another embodiment, a composition comprises N-M-A-N-A-K (SEQ ID NO: 1), at least one additional skin care additive, and a dermatologically suitable carrier. In yet another embodiment, a composition comprises N-M-A-N-A-K (SEQ ID NO: 1), a TGF-β mimic peptide, and a dermatologically suitable carrier.

Accordingly several advantages of one or more aspects are as follows: to provide a skin care composition that reverses the features of skin aging, that is comprised of components acting synergistically, that can easily be manufactured, and that is safe and easy to use. Other advantages of one or more aspects will be apparent from a consideration of the ensuing description.

STATEMENTS AS TO THE RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

The present application is being filed along with a Sequence Listing in electronic format. The Sequence Listing file entitled, GB0002USUTILSEQLST.txt, was created on 14 Mar. 2017 and is 1 KB in size. The information in electronic format of the Sequence Listing is incorporated herein by reference in its entirety.

BACKGROUND OF THE INVENTION

Currently, consumers have a wide variety of options—ranging from nonsurgical to surgical—aimed at combating the unwanted effects of aging skin and for furnishing a more youthful appearance. Nonsurgical methods include the topical use of moisturizers and keratolyic agents, cleansers, sunscreens and sunblocks, antioxidants, serums, exfoliants, and makeup. Surgical methods include chemical peels, the use of botulinum toxin or fillers (e.g., bovine collagen, silicone, and hyaluronic acid), and plastic or laser surgery. However, although the majority of the aforementioned alternatives provide at least one skin-care benefit, they are not without their drawbacks as well.

For example, many topical skin treatments contain ingredients that can clog pores, promote acne, trigger allergies, cause irritation, and block natural water evaporation, thereby disturbing the skin's normal healthy balance. Specifically, although retinoid therapy has shown promise in the treatment of skin-aging maladies, certain retinoids such as tretinoin and tazarotene, have been shown to cause burning, scaling, and dermatitis thereby limiting their acceptance by many patients. And because alpha hydroxy acids, a common additive to numerous skin care products, work mainly as an exfoliant whereby outer stratum epidermal cells are prematurely sloughed off, the resulting newly exposed cells are susceptible to irritation and sun sensitivity. Even ingredients as seemingly benign as emollients and moisturizers (e.g., mineral oil, petrolatum and lanolin), have been known to cause burning, stinging, redness, or irritation in some cases. Lastly, some commercially available compositions contain ingredients that are supported by pseudo-scientific claims, which are misleading or unsupported by scientific evidence, and are in fact hazardous to the skin.

Alternatively, although chemical peels help to improve the appearance of aging and dull skin by stimulating cell turnover and cell function in the layers just below the treated top layer of the skin, because acids are commonly used during the procedure, the patient may experience a burning sensation. And, depending on the compound used, recovery times may take up to four weeks during which the skin may ooze and scab. Finally, although not extremely common, the procedure can cause infection, permanent scaring or discoloration, and excessively dry skin that peels too often.

In addition, many modern treatments for aged skin—including the use of peptides and other actives that stimulate new collagen and connective tissue production—have been shown to have a limited temporary effect. As a result, once daily use has ceased, the skin will revert to its previous aged looking condition. Many of the limitations are a product of the peptide's reduced length, which in turn contributes to their generally poor specificity, their conformational flexibility, and their inability to fold into secondary, tertiary, and quaternary structures. Furthermore, peptides are hydrophilic. Therefore, they are unable to penetrate easily the lipophilic stratum corneum layer of the epidermis. Despite their hydrophilicity, however, peptides are generally unstable in water-based formulations, as the water breaks down the peptide bond, rendering it inactive. Moreover, should peptides be absorbed, the abundant presence of enzymes found in the skin can also break down peptide bonds.

In addition, recent scientific studies on normal skin renewal processes have shown that NF-κB plays an integral role in the turnover of skin tissues; human skin is always being turned over, that is renewed. And, NF-κB is in large part responsible for the removal of the old skin, so it can be replaced by the new skin. As the skin ages, the skin's natural homeostatic condition changes to that typified by an older skin phenotype, as compared to youthful phenotypes. One of the controlling factors is an increase in NF-κB, which causes the skin to look older, thinner, dryer, inflamed, and more wrinkled. This aging process is accelerated by many different environmental factors, including exposure to sunlight, pollution, low humidity, and smoke. These external insults cause disruption in the skin's normal homeostatic mechanisms, which accelerate the worsening appearance of aged looking skin.

In light of the deficiencies and drawbacks prevalent in the prior art, it is readily apparent that there continues to be a significant need for skin care compositions which not only improve and maintain the health and physical appearance of the skin but are also safe, stable, long-lasting, and effective in treating the appearance of wrinkles, fine lines, pores, discolorations, sallowness, and other forms of undesirable skin surface textures.

BRIEF DESCRIPTION OF THE SEVERAL VIEWS OF THE DRAWING

Not applicable.

DETAILED DESCRIPTION OF THE INVENTION

Found in almost all animal cell types, Nuclear Factor-kappa B (NF-κB) is a protein complex that controls transcription of DNA, cytokine production and cell survival. NF-κB has been found to be involved in cellular responses to stimuli such as stress, cytokines, free radicals, ultraviolet radiation, oxidized LDL, and bacterial and viral antigens. Incorrect regulation of NF-κB has been linked to cancer, inflammatory and autoimmune diseases, septic shock, viral infection, and improper immune development. Accordingly, agents that can inhibit or regulate NF-κB activation have the potential to treat a variety diseases and disorders, including the unwanted effects of aging skin.

The present invention relates to a novel amino acid sequence, N-M-A-N-A-K (SEQ ID NO: 1), designed and synthesized to inhibit NF-κB production and the use of N-M-A-N-A-K (SEQ ID NO: 1) in chemical compositions to revert aged skin to a more youthful state.

In one embodiment, the invention provides for the topical application of an effective amount of the NF-κB-inhibitor peptide, N-M-A-N-A-K (SEQ ID NO: 1), in a cosmetic composition to the skin of an individual. The cosmetic treatment is used to modulate a cosmetic condition such as skin aging, which can include but is not limited to wrinkling, uneven pigmentation, sagging, by reducing the underlying inflammatory cause. In some embodiments N-M-A-N-A-K (SEQ ID NO: 1) is used in combination with other cosmetic or dermatological agents and carriers.

In another embodiment, the invention provides for the topical application of a cosmetic composition comprising the NF-κB-inhibitor peptide, N-M-A-N-A-K (SEQ ID NO: 1), together with other peptides, such as A-N-V-A-E-N-A (SEQ ID NO: 2), that have been shown to enhance healthy looking skin by reducing inflammation and by improving skin moisture content and turgor, whilst "curing" wrinkles and fine lines prevalent in aged skin. In some embodiments, the multiple peptide compositions are used in combination with other cosmetic or dermatological carriers.

I. Structure and Activity

The methods and compositions of the invention relate to NF-κB-inhibitors. An NF-κB-inhibitor, as the term is used herein, includes a synthetic or naturally occurring mixture of two or more of these compounds that is capable of having at least one activity of NF-κB-inhibitors, as measured by one or more of the assays described herein.

II. Assay for Activity of NF-κB-Inhibitors

In a typical assay, a susceptible cell is exposed to tumor necrosis factor alpha (TNFα) resulting in the activation of NF-κB. The cells exposed may include human cell lines KBM-5 (chronic myeloid leukemia), H1299 (lung adenocarcinoma), and A293 (embryonic kidney carcinoma), all obtainable from the American Type Culture Collection (ATCC).

Numerous assays are available for measuring levels of NF-κB. Assays that may be used to assess NF-κB-inhibitor activity include:

(i) Measurement of NF-κB by gel shift or electrophoretic mobility shift assay as described by Kumar Ap, Garcia G. E., SlagaTJ.@Methoxyestradiol blocks cell-cycle progression at $G^2/M$ phase and inhibits growth of human prostate cancer cells. Mol Carcinog 2001; 3:111-124.

(ii) Reporter gene assays based on simultaneous detection of constitutive and induced NF-κB by TNF alpha. These assays are available in kit form commercially.

(iii) Assays based on Enzyme-linked immunosorbent assay available in kit form from numerous vendors.

A hexapeptide with a specific amino acid sequence has been found to function as an NF-κB-inhibitor in the methods provided herein. The present invention relates to the use of the peptide as an active ingredient in or for the preparation of a cosmetic and dermatological preparation where the sequence of the peptide is as given below:

Asparagine-Methionine-Alanine-Asparagine-Alanine-Lysine (Asn-Met-Ala-Asn-Ala-Lys)

Or using the newer amino acid nomenclature code system: N-M-A-N-A-K (SEQ ID NO: 1).

In this case, the "physical" structure and chemical shape confer amphiphilic properties to the peptide and enhance its ability to bind with proteinaceous substrates such as cell surface signaling antennae. Furthermore, N-M-A-N-A-K (SEQ ID NO: 1) can be derivatized by reacting it with other compounds, e.g., palmitoyl chloride, to vary its solubility and surface active properties.

The term amino acid as used herein means an organic compound containing both a basic amino group and an acidic carboxyl group. The amino acids are "natural", generally laevorotatory (or L) amino acids, which are known to occur biologically in free or combined form.

Natural Amino Acids include, but are not limited to, alanine, arginine, asparagine, aspartic acid, cysteine, glutamic acid, glutamine, glycine, histidine, isoleucine, leucine, lysine, methionine, phenylalanine, serine, threonine, tryptophan, proline and valine.

III. Synthesis of Peptide NF-κB-Inhibitors

The NF-κB-inhibitor peptides may be synthesized by any suitable method for producing peptides of a given sequence. Preferably, peptides of the present invention, specifically N-M-A-N-A-K (SEQ ID NO: 1) can be synthesized by various suitable methods that are well known in the art, preferably by solid phase synthesis, manual or automated, as first developed by Merrifield and described by Stewart et al. in "Solid Phase Peptide Synthesis" (1984). Specifically, chemical synthesis joins amino acids in the pre-determined sequence starting at the C-terminus (carboxyl). Basic solid phase methods require coupling the C-terminal protected alpha-amino acid to a suitable insoluble resin support. Amino acids for synthesis require protection on the alpha-amino group to ensure proper peptide bond formation with the preceding residue (or resin support). Following completion of the condensation reaction at the carboxyl end, the alpha-amino protecting group is removed to allow the addition of the next residue. Several classes of alpha-protecting groups have been described, see Stewart et al. in "Solid Phase Peptide Synthesis" (1984), with the acid labile, urethane-based tertiary-butyloxycarbonyl (Boc) being historically preferred. However, other protecting groups, such as the base labile 9-fluorenylmethyloxycarbonyl (FMOC) may be used. The complex array of functional blocking groups, along with strategies and limitations of their use, has been reviewed by Bodansky in "Peptide Synthesis" (1976) as well as by Stewart.

Solid phase synthesis is initiated by the coupling of the described C-terminal alpha-protected amino acid residue. Coupling requires activating agents such as dicyclohexycarbodiimide (DCC), with or without 1-hydroxybenzo-triazole (HOBT), diisopropylcarbodiimide (DIIPC) or ethyldimethylaminopropylcarbodiimide (EDC). After coupling the C-terminal residue, the alpha-amino acid protected group is removed by trifluoroacetic acid in dichloromethane in the case of the acid labile tertiary-butyloxycarbonyl (Boc) groups. A neutralizing step with triethylamine (10%) in dichloromethane recovers the free amine (versus salt). After the C-terminal-residue is added to the resin, the cycle of deprotection, neutralization and coupling is repeated in order to extend the protected peptide chain. Each protected amino acid is introduced in excess (three to fivefold) with equimolar amounts of coupling reagent in suitable solvent. Finally, after the completely blocked peptide is assembled on the resin support, reagents are applied to cleave the peptide from the resin and remove the side chain blocking groups. Anhydrous hydrogen fluoride (HF) cleaves the acid labile Boc chemistry groups. Several nucleophilic scavengers, such as dimethylsulfide and anise, are included to avoid side reactions, especially on amino acid side chain functional groups.

Slight modifications to the amino acid sequence, N-M-A-N-A-K (SEQ ID NO: 1), will not affect the peptides ability to inhibit NF-κB. Examples would include, but are not limited to, reacting N-M-A-N-A-K (SEQ ID NO: 1) with palmitoyl chloride or substituting methyl alanine for alanine in the sequence.

IV. Applications

The present invention has the wide applicability to a host of cosmetic conditions. The mode of administration for cosmetic applications is typically topical, but administration and dosage regimens will vary depending on the cosmetic condition whose modulation is sought.

The present invention provides compositions for cosmetic use by individuals (humans, specifically). The embodiments are used to provide a topical cosmetic treatment to the skin where treatment for aging (lines and wrinkles), dryness, loss of suppleness, turgor and to repair damage done by UV light, pollutants, etc. Cosmetic benefits include a reduction in lines and wrinkles, reduction in skin dryness, a normalization of natural skin oiliness, conditions associated with aging skin. Additional improvements include a reduction in redness, inflammation and soreness. These cosmetic improvements are accompanied by an amelioration of the psychological consequences of aging. An NF-κB-inhibitor provides long term benefits, not only eradicating issues associated with aged skin, but providing long term improvement in skin vitality.

NF-κB is continually produced by cells as a part of the general "repair mechanisms" as they cope with damage and deterioration from daily living and aging. Older tissues show higher levels of NF-κB than juvenile tissues. The presence of more NF-κB is asymptotic of older skin, and is associated with higher levels of inflammation, stress related aging symptoms. Higher levels of NF-κB are a result of a slowdown of normal healthy cell metabolism. The key here is not to ensure that all NF-κB is inhibited but that it is reduced to levels seen in healthy younger skin. NF-κB is present as a part of the normal cellular aging turnover, repair mechanisms, and apoptosis. Skin cells (epidermal) are turned over every 21 to 28 days; as one ages, this rate slows down. The presence of aged skin is associated with more NF-κB and higher levels of inflammation and associated disorders (dryer, more wrinkled, thinner looking skin).

Use of an NF-κB-inhibitor, such as N-M-A-N-A-K (SEQ ID NO: 1), at an effective level will modulate the cellular inflammation process, by reducing it. As a consequence the skin's overall condition will be improved. N-M-A-N-A-K (SEQ ID NO: 1) will help return the skin's general metabolic activity, as measured by the amount of NF-κB, to conditions seen in younger looking (juvenile) skin. However, some measure of NF-κB in the skin cells is essential to maintain healthy looking youthful skin; elimination is contra-indicated.

An NF-κB-inhibitor provides a cosmetic benefit not only when a cosmetic defect (such as skin redness) is eradicated. The compositions of the invention may be directed at achieving a "prophylactic" or "preventative" effect, including prevention of a condition, retarding the progress of a skin condition (e.g., aging), or decreasing the likelihood of occurrence of a condition. As used herein, "treating" or treatment includes prophylaxis.

As used herein, the effective amount encompasses an amount sufficient to effect beneficial or desired cosmetic results. An effective amount can be administered in one or more administrations. In terms of cosmetic treatment, an "effective amount" of an NF-κB-inhibitor of the invention is an amount that is sufficient to palliate, ameliorate, stabilize, reverse or slow the progression of a cosmetic condition, or to provide a desired effect such as cosmetic augmentation (enhanced plumpness) of soft tissue. An "effective amount" may be of an NF-κB-inhibitor alone or in conjunction with one or more agents used to modulate a cosmetic condition.

Moreover, the skin is subject to a number of cosmetic conditions that result in alterations of function and/or appearance that are considered undesirable, and whose manifestation can lead to psychological discomfort as well as possible physiological discomfort or harm. Cosmetic treatments are used even when no obvious visible defect is present, as it is desirable to the individual to augment or alter the skin in such a way as to produce a cosmetically pleasing effect. Users are remarkably perceptive in seeing changes in the way the skin appears and feels to them, such as enhanced radiance and softness, typical of healthy skin.

Exemplary cosmetic conditions that may be modulated by the invention include, but are not limited to, skin aging, cosmetic defects, undesired pigmentation, and reduction in redness (inflammation).

As used herein, "skin aging" refers to alterations in the appearance and function of skin that occur with aging, such as wrinkling, loss of elasticity, sagging, uneven pigmentation and loss of underlying tissue mass. As the skin ages there is a decrease in cell proliferation and in cell function. Such conditions can be accelerated and exacerbated by exposure to UV radiation, whereby the epidermis thins and the skin appendages atrophy. Furthermore, the skin's hair follicles become sparser and sebaceous secretions decrease, with consequent susceptibility to dryness, chapping and fissuring. The dermis diminishes with loss of elastic fibers and collagen fibers, and keratinocyte proliferation—indicative of skin thickness and skin proliferative capacity—decreases with age.

An increase in keratinocyte proliferation and collagen production has been shown to counteract many aspects of skin aging, i.e., lines and wrinkles, thickness, elasticity and repair. According the present invention, an NF-κB-inhibitor can be used cosmetically to counter-act, at least whilst being correctly used, the effects of aging on skin. A cosmetic formulation containing an NF-κB-inhibitor may be applied topically in areas where it is desired to counteract skin aging.

Also included in the skin conditions that may be treated by the invention are cosmetic defects that, while not pathological or physiologically harmful, may nonetheless cause psychological distress, in some cases to the extreme. In these cases it is desirable to correct a particular feature or features causing distress or, alternatively, enhance a feature considered desirable. In addition to aging skin, such conditions include, e.g. striae gravidorum and striae distensiae (stretch marks), atrophic scarring, thickened and cracked skin, often associated with pre-diabetic and diabetes (especially on the feet), and hair loss.

One aspect of the invention relates to enhancing hair growth. Cells from which hair is produced grow in the bulb of the follicle. They are extruded in the form of fibers as the cells proliferate in the follicle. Hair "growth" refers to the formation and elongation of the hair fiber by the dividing cells. Some embodiments of the invention provide a means for altering the dynamics of the hair growth cycle to induce proliferation of hair follicle cells, particularly the stem cells of the hair follicle. The size of the "hair" produced generally depends on the size of the follicle, which is regulated, to some extent, by the number and rate of proliferation of follicle stem cells. One embodiment of the invention, comprises administering to the skin in the area in which hair growth is desired an amount of an NF-κB-inhibitor peptide in conjunction with a peptide designed to bind to the TGF-β receptor-1s. Specifically, the heptapeptide, A-N-V-A-E-N-A (SEQ ID NO: 2), will help to increase hair follicle size, by repairing inflammation, caused by extraneous effects, and by normalizing the amount of NF-κB consistent with healthy cell metabolism. This cosmetic treatment can be used in conjunction with an FDA approved active, such as 5% minoxidil, for superior results.

Typically, the composition will be applied on a daily basis until hair growth is observed, and thereafter sufficiently to maintain the desired amount of hair growth.

The invention also relates to treating undesired pigmentation, which relates specifically to pigmentation over an area of the body that is different than the pigmentation desired by the individual. Undesired pigmentation can be a result of photo aging, reaction to inflammation, or reaction to trauma such as surgical or accidental skin breakage. Undesired pigmentation includes small areas such as freckles, fade spots, etc.

Another aspect of the invention relates to cosmetic treatment to provide lip enhancement. The structure of the lips is different than that of the skin, but it is subject to similar aging issues, e.g., chronic damage from UV exposure, dryness, soreness, and cracking. A suitable cosmetic lip product containing an NF-κB-inhibitor, either alone or combined with other previously described cosmetic actives, will enhance the return to more youthful healthy looking conditions, by reducing cracking and dryness, when applied to them on a daily basis.

The preferred embodiment of the invention is a skin care composition comprising the hexapeptide NF-κB-inhibitor with the sequence N-M-A-N-A-K (SEQ ID NO: 1) or its palmitoyl derivative. Application of N-M-A-N-A-K (SEQ ID NO: 1) alone, helps to restore the skin cells to a more youthful homeostatic state by modulating the release of NF-κB, so it is consistent with levels required to maintain healthy tissue. This process takes time and is restrained in its effectiveness when inflammatory conditions are encountered. The addition to the skin care composition of a TGF-β1 peptide mimic, such as A-N-V-A-E-N-A (SEQ ID NO: 2), which binds to the cell receptors responsible for cellular healing, will help to clear up the excess inflammatory issues associated with aging skin. This allows the NF-κB-inhibitor, N-M-A-N-A-K (SEQ ID NO: 1), to quickly control the on-going inflammatory cascade, helping to quickly restore the skin tissues a state associated with youthful, juvenile looking skin.

Expression levels for a variety of different genes treated with N-M-A-N-A-K (SEQ ID NO: 1) and A-N-V-A-E-N-A (SEQ ID NO: 2) were determined using DNA microarray analysis of cultured human fibroblasts at BioInnovation Laboratories, Inc., Lakewood, Colo.

The microarrays were scanned with an Axon GenePix 4100A Scanner with the scanning resolution set to 10 μm and analyzed with GenePix Pro software. During the initial scan the PMT gains for the scanner were adjusted such that the Cy5/Cy3 image count ratios were between 0.9 and 1.1.

To derive the standard curve for the assay, the relative fluorescent units versus the known RNA concentrations in μg/ml for the standards were plotted and subjected to regression analysis to establish the line that best fit the data points. Mean RFU values for the test materials and untreated samples were used to estimate the amount of RNA present in each sample.

Because the level of gene expression is related to the fluorescence intensity of the probed gene marker on the microarray, and since it is possible to have differences in labeling efficiency when making the Cy3 and Cy5 probes, it is essential to normalize the fluorescence measurements between the two respective dyes before examining changes in gene expression. As a result, fluorescence intensities for the microarrays were subjected to global normalization. The total fluorescent signal for both dyes was normalized with a correction factor so that the ratio of total intensities for both dyes was equal to one.

The resulting normalized total fluorescent signals for peptides, N-M-A-N-A-K (SEQ ID NO: 1) and A-N-V-A-E-N-A (SEQ ID NO: 2) with a variety of gene samples are shown in Table 1.

TABLE 1

Upregulation of Genes in Human Fibroblasts Treated with Peptides (10 ppm)

| Gene Class/Name | Peptide Fluorescent Intensity ||
|---|---|---|
| | ANVAENA (SEQ ID NO: 2) | NMANAK (SEQ ID NO: 1) |
| TGF Family Molecules | | |
| TGFB | 0.113 | 1.224 |
| TGFBR1 | 0.128 | 0.373 |
| TGFBR2 | 0.040/1.482 | — |
| TGFBR3 | 0.098 | 1.229 |
| Extracellular Matrix Genes Regulated by TGF Beta | | |
| COL1A1 | 2.198 | — |
| COL4A1 | 0.910 | — |
| Fibronectin | 1.407 | — |
| COL1A2 | 3.669 | 3.992 |
| COL3A1 | 2.987 | 2.047 |
| COL6A1 | 6.282 | 3.446 |
| COL6A2 | 2.902 | 1.705 |
| COL7 | 0.435 | 1.080 |
| βIG-H3 (TGFBI) | 2.069 | — |
| IL-6 | 1.135 | — |
| EGFR | 1.133 | 1.159 |
| PDGFR alpha subunit | 1.330 | 1.608 |
| Tenascin (TNXB) | 1.353 | 1.752 |
| CTGF | 0.076 | 0.429 |
| ELN | — | 0.773 |

TABLE 1-continued

Upregulation of Genes in Human Fibroblasts
Treated with Peptides (10 ppm)

| | Peptide Fluorescent Intensity | |
|---|---|---|
| Gene Class/Name | ANVAENA (SEQ ID NO: 2) | NMANAK (SEQ ID NO: 1) |
| ELA2A (elastase) | — | 3.148 |
| MMP1 | 1.991 | 1.164 |
| MMP2 | 0.034 | 0.785 |
| TIMP1 | 4.567 | 4.057 |
| BMP7 | — | 2.000 |
| FGF3 (fibroblast growth factor) | — | 2.000 |
| TGF Beta Signaling Pathway Molecules | | |
| Smad1 | 1.325 | 0.918 |
| Smad3 | 1.202 | 0.882 |
| Smad2 | 0.824 | 0.857 |
| Smad4 | 0.374 | 0.454 |
| SP1 | 0.590 | 0.932 |
| PAI1 | Not Listed | — |
| SAR1A | 1.905 | 1.632 |
| Smad7 | 0.357 | 1.160 |
| Smad6 | 0.136 | 1.354 |
| p300 (EP300) | 0.961 | — |
| CBP (CREBBP) | 0.375 | 0.743 |
| p38MAPK (MAPK14) | 0.594 | 1.057 |
| Molecules that Regulate TGF Beta Expression/Activity | | |
| YY1 | 0.713 | 1.378 |
| BMP1 | 0.497 | 0.837 |
| LTBP (LTBP1) | 0.652 | 0.268 |
| MMP2 | 0.034 | — |
| Activin A beta subunit (INHBB) | 0.261 | 0.095 |
| Inhibin (INHA) | 0.264 | 1.917 |
| Follistatin (FST) | 0.594 | 0.665 |
| Genes that Regulate Wound Healing (regulated by TGF beta) | | |
| VEGFA | 0.798 | 1.385 |
| FGF2 | 0.912 | 0.679 |
| GM-CSF (CSF2) | 0.014 | — |
| Additional Genes | | |
| LOX | 0.974 | 1.035 |
| OGG1 | 1.364 | 1.176 |
| PLOD | 1.112 | 1.105 |
| PLOD2 | 0.445 | 1.085 |
| PLOD3 | 3.805 | 4.092 |
| RAD23A | 0.078 | 0.933 |
| RAD23B | 1.218 | 0.603 |
| SIRT1 | 0.228 | 0.410 |
| SIRT3 | 0.010 | 0.735 |
| SIRT 5 | — | 1.482 |
| TERT | 0.198 | — |
| AQP3 | — | 3.294 |
| EEF1A1 (cell growth) | — | 6.301 |
| EEF1A2 (cancer cell growth) | — | 0.067 |
| EEF1G (aminoacyl transferase - glutathione) | — | 1.928 |
| Anti-Inflammatory | | |
| COX1 | — | 2.645 |
| COX411 | — | 2.067 |
| COX7C | — | 1.341 |
| COX8A | — | 1.803 |
| DEFB4 | — | 4.798 |
| IL10RB | — | 1.889 |
| IL26 | — | 2.036 |
| IL27 | — | 2.257 |
| ILF2 | — | 4.120 |
| ILDR1 (immunoglobin receptor) | — | 1.546 |

As illustrated by Table 1, treatment of the fibroblasts with 10 ppm of the peptide N-M-A-N-A-K (SEQ ID NO: 1) resulted in the upregulation of several genes responsible for expressing extra-cellular matrix components including collagen production genes COL1A2, COL3A1, COL6A1 and COL6A2. Also of particular importance is the impact N-M-A-N-A-K (SEQ ID NO: 1) has on anti-inflammatory genes. At least ten (10) of these genes, which would be reduced in activity by the presence of excess NF-κB in the cell, are upregulated. As shown in Table 1, these genes include COX1, COX411, COX7C, COX8A, DEFB4, IL10RB, IL26, IL27, ILF2 and ILDR1. By upregulating these anti-inflammatory genes, N-M-A-N-A-K (SEQ ID NO: 1) inhibits interleukins (IL) and tumor necrosis factors (TNF), both often found in irritated, inflamed skin. As a result, inflamed skin will calm or become normalized, thereby keeping NF-κB levels normal for healthy skin homeostasis. This is particularly important for sun-damaged skin whereby some of the receptors needed for TGF-β activation of cell repair have been damaged by ultraviolet light.

Other genes important for skin health that are upregulated by N-M-A-N-A-K (SEQ ID NO: 1) include AQP3 (aquaporin3), a key to water content in the skin, as well as EEf1G (glutathione), a potent antioxidant and cell protector.

Table 1 also shows a similar but broader range of genes was upregulated by the peptide A-N-V-A-E-N-A (SEQ ID NO: 2). Since multiple pathways exist for cells to be stimulated to produce collagen and other connective tissue components, a synergistic and complementary effect results with the two peptides, N-M-A-N-A-K (SEQ ID NO: 1) and A-N-V-A-E-N-A (SEQ ID NO: 2) in the skin care composition. Moreover, N-M-A-N-A-K (SEQ ID NO: 1) further complements TGF-β mimics such as A-N-V-A-E-N-A (SEQ ID NO: 2) by upregulating genes, such as YY1 and INHA, that control TGF-β expression.

Additionally, since A-N-V-A-E-N-A (SEQ ID NO: 2) alone does not impact anti-inflammatory genes significantly, the two peptides, N-M-A-N-A-K (SEQ ID NO: 1) and A-N-V-A-E-N-A (SEQ ID NO: 2) in tandem, reduce inflammation and stimulate new collagen—as well as provide for other important repair mechanisms in the skin—and extensively reverse the features of skin aging.

The NF-κB-inhibitor, N-M-A-N-A-K (SEQ ID NO: 1), may be administered in any cosmetically acceptable carrier, subsequently described in more detail. In embodiments of methods of the invention, the concentration of the N-M-A-N-A-K (SEQ ID NO: 1) used can range from 0.00001% (0.1 ppm) through 5.0%. The preferred range is 0.0001% (1 ppm) through 0.001% (100 ppm).

Skin coverage by N-M-A-N-A-K (SEQ ID NO: 1) is represented in $ng/cm^2$. In these terms, a typical coverage per administration would be between 3 to 600,000 $ng/cm^2$.

The methods of the invention typically utilize topical administration, which may be by any suitable means that brings the NF-κB-inhibitor N-M-A-N-A-K (SEQ ID NO: 1) and, optionally other cosmetic and dermatological agents, in contact with the surface of the skin, including application as a gel, lotion or cream, liposomal or other suitable delivery system, with or without occlusion, or application as a plaster, patch, mask, glove, or similar device for extended contact with an area of skin under treatment. For modulation of cosmetic conditions or to produce a desired cosmetic effect, the frequency and duration of administration of a formulation containing N-M-A-N-A-K (SEQ ID NO: 1) is dependent on many factors, including the nature of the formulation, presence of other cosmetic or dermatological agents, vehicle type, the severity and extent of the condition, and in some cases the judgment of a skin care professional (such as a dermatologist or a cosmetologist).

As the skin is subject to continual turnover as it combats exposure to the environment. Typical cosmetics are "sloughed" off in the insensible invisible skin flakes continually lost from the skin's surface in a two to four hour time frame. Hence, unless a cosmetic vehicle is designed to provide a longer lasting surface effect, it is important to re-apply any skin treatment several times a day to ensure that the skin appears improved. Hence with formulations containing N-M-A-N-A-K (SEQ ID NO: 1) designed for topical treatment and to restore youthful homeostatic conditions, by reducing inflammatory cytokines such as NF-κB, need to be used daily, with re-application to the skin as many as 2-4 times a day. It is perfectly acceptable to use N-M-A-N-A-K (SEQ ID NO: 1) with other cosmetic formulations, such as sunscreens, make-up, etc.

The duration of the treatment will to some extent depend on the response of the skin to the cosmetic treatment in the method of invention. When skin ages, the actual homeostatic conditions do change. NF-κB is just one measure of these permanent changes. For compositions containing an NF-κB-inhibitor, like N-M-A-N-A-K (SEQ ID NO: 1), continual daily use, almost as a prophylactic, is required to maintain skin homeostasis typical of youthful skin. Hence, the vehicle selected should spread easily into the skin, be light and pleasing, non-oily, non-greasy and refreshing when used. Typically an emulsion vehicle based on uniform droplet size will be absorbed easily into the skin and feel comfortable. Modifications of frequency and duration are easily accomplished by the individual using the method of invention.

Some embodiments of cosmetic treatment of the skin can be formulated using a wide range of cosmetic ingredients. Examples of commonly used cosmetic materials, include, but are not restricted to: emulsifiers (e.g. quaternary cationic, anionic, non-ionic), emollients (e.g., esters, vegetable oils), humectants (e.g., glycerin), lanolin derivatives, petrolatum, mineral oil, silicones (e.g., dimethicone, cyclomethicones), thickeners (e.g., guar gum, polyacrylate gums). A cosmetic formulation with great aesthetics and functionality can be assembled by one skilled in the art. The NF-κB-inhibitor, N-M-A-N-A-K (SEQ ID NO: 1) and its derivatives, e.g., Pal-N-M-A-N-A-K as incorporated, can be varied between 0.0001% and 5%. A cosmetic lotion containing 0.001% N-M-A-N-A-K (SEQ ID NO: 1) is used at a frequency of once to four times a day, until the desired result, a reduction in lines and wrinkles, in the skin's appearance is observed.

Formulations containing NF-κB-inhibitor N-M-A-N-A-K (SEQ ID NO: 1) may be used in conjunction with other "active" cosmetic ingredients, such as retinoids, ascorbic acid, niacin, cholecalciferol, antioxidants (e.g. super oxide dismutase, tocopherols, polyphenols, ubiquinonol), hydroxy acids, peptides (e.g. Pal-GHK, Cu-GK, etc.). It is possible to administer them in conjunction with N-M-A-N-A-K (SEQ ID NO: 1) in the same formula, or, the two may administered simultaneously, consecutively, in overlapping durations, similar, the same or different frequencies, etc.

V. Compositions

The compositions of the present invention may contain at least one additional ingredient in addition to the NF-κB-inhibitor peptide, N-M-A-N-A-K (SEQ ID NO: 1). Moreover, the compositions of the present invention may contain a multitude of additional ingredients.

A. Additional Skin Care Actives

For example, the compositions of the present invention may include various other and additional ingredients, which may be active, functional, and conventionally used in cosmetic, personal care, or topical/transdermal products or otherwise. Naturally, a decision to include an additional ingredient or additional ingredients depends on the specific application and product formulation for the composition.

Thus, the compositions of the present invention may include one or more additional ingredients, which provide some benefit to the object of the composition. Such additional ingredients may include one or more substances, without limitations, such as: cleaning agents, hair conditioning agents, skin conditioning agents, hair styling agents, antidandruff agents, hair growth promoters, perfumes, sunscreen and/or sunblock compounds, pigments, moisturizers, film formers, hair dyes, make-up agents, detergents, pharmaceuticals, thickening agents, emulsifiers, humectants, emollients, antiseptic agents, deodorant actives, dermatologically acceptable carriers, and surfactants. In one embodiment, where the composition is to be in contact with human skin, the additional ingredients should be suitable for application to human skin, that is, when incorporated into the composition they are suitable for use in contact with human skin without undue toxicity, incompatibility, instability, allergic response, and the like within the scope of sound medical judgment. The *CFTA Cosmetic Ingredient Handbook*, Ninth Edition (2002) describes a wide variety of non-limiting cosmetic and pharmaceutical ingredients commonly used in the skin care industry, which are suitable for use as additional ingredients in the compositions of the present invention. Non-limiting examples of these additional ingredient classes include: abrasives, adsorbents, aesthetic components such as fragrances, pigments, colorings/colorants, essential oils, skin sensates, astringents, (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropynyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, i.e., polymers for aiding the film-forming properties and substantivity of the composition (e.g., copolymer of eicosine and vinyl pyrolidone), opacifying agents, pH adjusters, propellants, reducing agents, sequestrants, skin bleaching and lightening agents (e.g., hydroquinone, kojic acid, ascorbic acid, magnesium ascorbyl phosphate, and ascorbyl glucosamine), skin-conditioning agents, (e.g., humectants, including miscellaneous and occlusive), skin soothing and/or healing agents (e.g., panthenol and its derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or to those particular applications listed.

1. Farnesol

The topical compositions of the present invention may contain a safe and effective amount of farnesol. Farnesol is an organic compound produced by both plants and animals. Farnesol is involved in protein modification and regulation (e.g., farnesylation of proteins), while derivatives of farnesol act as a precursor and/or intermediate in the biosynthesis of squalene, which in turn is a precursor for steroids in plants, animals and fungi. As a result, farnesol and its derivatives are important starting compounds for both natural and artificial organic synthesis.

Farnesol is a present in many essential oils such as citronella, lemon grass, rose, musk and balsam. It is used commonly in perfumes as a co-solvent that regulates the volatility of the odorants. Farnesol is used also as a deodorant in cosmetic products due to its anti-bacterial activity.

Chemically, farnesol is [2E, 6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco, 10 Gordon Drive, Totowa, N.J.) and trans-trans-farnesol (Sigma Chemical Company, P.O. Box 14508, St. Louis, Mo.).

When present in the compositions of the present invention, the composition preferably contains from about 0.001% to about 50% by weight of the composition, more preferably from about 0.01% to about 20%, even more preferably from about 0.01% to about 15%, even more preferably from about 0.1% to about 10%, still more preferably from about 0.5% to about 5% and still more preferably from about 1% to 5% of farnesol.

2. Phytantriol

The topical compositions of the present invention may contain a safe and effective amount of phytantriol. Phytantriol is the common name for the chemical know as 3,7,11,15-tetramethylhexadecane-1,2,3-triol. Phytantriol is commercially available from BASF (1609 Biddle Avenue, Wyandotte, Mich.). For example, phytantriol is useful as a spider vessel/red blotchiness repair agent, a dark circle/puffy eye repair agent, sallowness repair agent, a sagging repair agent, an anti-itch agent, a skin thickening agent, a pure reduction agent, an oil/shine reduction agent, a post-inflammatory hyperpigmentation repair agent, a wound treatment agent, an anti-cellulite agent, and for regulating skin texture, including wrinkles and fine lines.

In the compositions of the present invention, the phytantriol is preferably included in an amount from about 0.001% to about 50% by weight of the composition, more preferably from about 0.01% to about 20%, even more preferably from about 0.1% to about 15%, even more preferably from about 0.2% to about 10%, still more preferably from about 0.5% to about 10%, and still more preferably from about 1% to 5% of phytantriol.

3. Desquamation Actives

A safe and effective amount of desquamation active may be added to the compositions of the present invention, more preferably from about 0.1% to about 10%, even more preferably from about 0.2% to about 5%, also preferably from about 0.5% to about 4%, by weight of the composition. Desquamation actives enhance the skin appearance benefits of the present invention. For example, the desquamation actives tend to the texture of the skin (e.g., smoothness). One desquamation system that is suitable for use herein contains sulfhydryl compounds and zwitterionic surfactants and is described in U.S. Pat. No. 5,681,852 to Bisset, incorporated herein by reference. Another desquamation system that is suitable for use herein contains salicylic acid and zwitterionic surfactants and is described in U.S. Pat. No. 5,652,228 issued to Bisset, incorporated herein by reference. Zwitterionic surfactants such as described in these applications are also useful as desquamatory agents herein, with cetyl betaine being previously preferred.

4. Enzymes, Enzyme Inhibitors and Enzyme Activators (Coenzymes)

The compositions of the present invention may contain a safe and effective amount of one or more enzymes, enzyme inhibitors or enzyme activators (coenzymes). Examples of enzymes are lipases, catalase, superoxidedismutase, amylases, glucuronidases, peroxidases, in particular glutathione peroxidase or lactoperoxidase, ceramidases, and hyaluronidases. All of these enzymes may be obtained by extraction or by fermentation biotechnology processes. Examples of enzyme inhibitors include trypsin inhibitors, Bowman Birk inhibitors, chymotrypsin inhibitors, botanical extracts with or without tannins, flavonoids, and quercetin which inhibit enzymatic activity. Enzyme preparations can be found, for instance, in the product named VENUCEANE proposed by SEDERMA, France (WO 02/066668 of Aug. 28, 2002). Enzyme activators and coenzymes include coenzyme A, coenzyme Q10 (ubiquinone), glycyrrhizidine, berberine and chrysine.

5. Botanical Extracts and Marine Extracts

The compositions of the present invention may contain a safe and effective amount of one or more extracts obtained from vegetable or marine sources. These extracts may be obtained by standard extraction processes and may be used in powder, paste, balm, oil or liquid (i.e., solution) form, preferentially as hydroglycolic extracts of terrestrial plants or marine plants, such as seaweeds, algae, and microalgae.

6. Anti-Acne Actives

The compositions of the present invention may contain a safe and effective amount of one or more anti-acne actives. Examples of useful anti-acne actives include resorcinol, sulfur, salicylic acid, benzoyl peroxide, erythromycin, zinc, etc. Further examples of suitable anti-acne actives are described in further detail in U.S. Pat. No. 5,607,980 issued to McAtee et al., on Mar. 4, 1997.

7. Anti-Wrinkle Actives/Anti-Atrophy Actives

The compositions of the present invention may further contain a safe and effective amount of one or more anti-wrinkle actives or anti-atrophy actives. Exemplary anti-wrinkle/anti-atrophy actives suitable for use in the compositions of the present invention include sulfur containing D and L amino acids and their derivatives and salts, particularly the N-acetyl derivatives, a preferred example of which is N-acetyl-L-cysteine; thiols (e.g., ethane thiol); hydroxy acids (e.g., alpha hydroxy acids such as lactic acid and glycolic acid or beta hydroxy acids such as salicylic acid and salicylic acid derivatives such as the octanoyl derivative), phytic acid, lipoic acid; lysophosphatidic acid, skin peel agents (e.g., phenol and the like), vitamin $B_3$ compounds and retinoids which enhance the keratinous tissue appearance benefits of the present invention, especially in regulating keratinous tissue condition, e.g., skin condition.

a) Vitamin $B_3$ Compounds

The compositions of the present invention may contain a safe and effective amount of a vitamin $B_3$ compound. Vitamin $B_3$ compounds are particularly useful for regulating skin condition as described in U.S. Pat. No. 5,939,082 issued to Oblong et al., on Aug. 17, 1999. When vitamin $B_3$ compounds are present in the compositions of the instant invention, the compositions preferably contain from about 0.01% to about 50%, more preferably from about 0.1% to about 10%, even more preferably from about 0.5% to about 10%, and still more preferably from about 1% to about 5%, still more preferably from about 2% to about 5%, by weight of the composition, of the vitamin $B_3$ compound.

As used herein, "vitamin $B_3$ compound" means a compound having the formula:

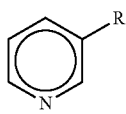

wherein R is —CONH$_2$ (i.e., niacinamide), —COOH (i.e., nicotinic acid) or —CH$_2$OH (i.e., nicotinyl alcohol); derivatives thereof; and salts of any of the foregoing.

Exemplary derivatives of the foregoing vitamin B$_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

Examples of suitable vitamin B$_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

b) Retinoids

The compositions of the present invention may also contain a retinoid. As used herein, "retinoid" includes all natural and/or synthetic analogs of vitamin A or retinol-like compounds which posses the biological activity of vitamin A in the skin as well as the geometric isomers and stereoisomers of these compounds. The retinoid is preferably retinol, retinol esters (e.g., C$_2$-C$_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate, [tocopherol ester of retinoic acid (trans- or cis-)], adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof.

The retinoid may be included as the substantially pure material, or as an extract obtained by suitable physical and/or chemical isolation from natural (e.g., plant) sources. The retinoid is preferably substantially pure, more preferably essentially pure.

The composition of this invention may contain a safe and effective amount of the retinoid, such that the resultant composition is safe and effective for regulating overall skin condition, preferably for regulating visible and/or tactile discontinuities in skin texture associated with skin aging. The compositions preferably contain from about 0.005% to or about 2%, more preferably 0.01% to or about 2%, by weight of the composition, of the retinoid. Retinol is preferably used in amount of from or about 0.01% to or about 0.15%; retinol esters are preferably used in an amount of from or about 0.01% or about 2% (e.g., about 1%); retinoic acids are preferably used in an amount of from about 0.01% to or about 0.25%; tocopheryl-retinoate, adapalene, and tazarotene are preferably used in an amount of from or about 0.01% to or about 2%.

Where the compositions of the present invention contain both a retinoid and a Vitamin B$_3$ compound, the retinoid is preferably used in the above amounts, and the Vitamin B$_3$ compound is preferably used in an amount of from or about 0.1% to or about 10%, more preferably from or about 2% to or about 5%.

c) Hydroxy Acids

The compositions of the present invention may contain a safe and effective amount of a hydroxy acid. Preferred hydroxy acids for use in the compositions of the present invention include salicylic acid and salicylic acid derivatives. When present in the compositions of the present invention, salicylic acid is preferably used in an amount of from about 0.01% to about 50%, more preferably from about 0.1% to about 20%, even more preferably from 0.1% to about 10%, still more preferably from about 0.5% to about 5%, and still more preferably from about 0.5% to about 2%.

8. Peptides

Additional peptides, including but not limited to di-, tri-, and tetrapeptides and derivatives thereof, may be included in the compositions of the present invention in amounts that are safe and effective. As used herein, "peptide" refers to both the naturally occurring peptides and synthesized peptides. Also useful herein are naturally occurring and commercially available compositions that contain peptides.

Suitable dipeptides for use herein include Carnosine® (beta-ala-his). Suitable tripeptides for use herein include gly-his-lys, arg-lys-arg, his-gly-gly. Preferred tripeptides and derivatives thereof include palmitoyl-gly-his-lys, which may be purchased as Biopeptide CL® (100 ppm of palmitoyl-gly-his-lys commercially available from Sederma, France); Peptide CK (arg-lys-arg); Peptide CK+ (ac-arg-lys-arg-NH$_2$); and a copper derivative of his-gly-gly-sold commercially as lamin, from Sigma Chemical Company (St. Louis, Mo.). Suitable tetrapeptides for use herein include Peptide E, arg-ser-arg-lys (SEQ ID NO: 3).

Preferably, the additional peptide is selected from palmitoyl-gly-his-lys, beta-ala-his, and their derivatives, and combinations thereof. More preferably, the additional peptide is selected from palmitoyl-gly-his-lys, their derivatives, and combinations thereof.

When included in the present compositions, the additional peptides are preferably included in amounts of from about $1\times10^{-6}$% to about 19%, more preferably from about $1\times10^{-6}$% to about 0.1%, even more preferably from about $1\times10^{-5}$% to about 0.01%, by weight of the composition. In certain embodiments which include the peptide, Carnosine®, the compositions preferably contain from about 0.1% to about 5%, by weight of the composition, of such peptides. In other embodiments wherein the peptide-containing composition Biopeptide CL® is included, the resulting composition preferably contains about 0.1% to about 10%, by weight of the composition, of the Biopeptide CL®.

9. Anti-Oxidants/Radical Scavengers

The compositions of the present invention may include a safe and effective amount of an anti-oxidant/radical scavenger. The anti-oxidant/radical scavenger is especially useful for providing protection against UV radiation which can cause increased scaling or texture changes in the stratum corneum and against other environmental agents, which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lysine pidolate, arginine pilolate, nordihydroguaiaretic acid, bioflavonoids, curcumin, lysine, methionone, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical composition and applicable to the present invention is described in U.S. Pat. No. 4,847,071, issued on Jul. 11, 1989 to Bisset et al.

10. Chelators

The compositions of the present invention may also contain a safe and effective amount of a chelator or chelating agent. As uses herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents, which can cause skin damage.

A safe and effective amount of a chelating agent may be added to the composition of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; U.S. Pat. No. 5,462,963, issued Oct. 31, 1995 to Bush et al.; and U.S. Pat. No. 5,364,617, issued Nov. 15, 1994 to Bush et al. Preferred chelators useful in compositions of the subject invention are furildioxime, furilmonooxime, and derivatives thereof.

11. Flavonoids

The compositions of the present invention may optionally contain a flavonoid compound. Flavonoids are broadly disclosed in U.S. Pat. Nos. 5,686,082 and 5,686,367, both of which are herein incorporated by reference. Flavonoids suitable for use in the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromoanones; one or more chromanols; isomers (e.g., cis/trans isomers) thereof; and mixtures thereof. The term "substituted" as used herein means flavonoids wherein one or more hydrogen atom of the flavonoid has been independently replaced with a hydroxyl, a $C_1$-$C_8$ alkyl, a $C_1$-$C_4$ alkoxy, or a O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones, (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy napthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones, (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4dihydroxy chalcone, and mixtures thereof. More preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

The herein described flavonoid compounds are preferably present in the subject invention at concentrations from about 0.01% to about 20%, more preferably from about 0.1% to about 10%, and still more preferably from about 0.5% to about 5% of the composition.

12. Anti-Inflammatory Agents

A safe and effective amount of anti-inflammatory agent may be added to the composition of the present invention, preferably from about 0.1% to about 10%, more preferably from about 0.5% to about 5%, of the composition. The anti-inflammatory agent enhances the skin-appearance-benefits of the present invention, i.e., such agents contribute to a more uniform and acceptable skin tone and color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionated, clobetasol valerate, desonide, desoxymethasone, desoxycorticosterone acetate, dexamethasone, dichlorisone, diflorasone diacetate, diflucortolone valerate, fluadrenolone, fluclorolone acetonide, fluocinonide, flucortine butylesters, fluocortolone, fluprednidene (fluprednylidene) acetate, flurandrenolone, halcinonide, hydrocortosine acetate, hydrocortosine butyrate, methylprednisolone, triamcinolone acetonide, cortisone, cortodoxone, flucetonide, fludrocortisone, fludrocortisone, difluorosone diacetate, fluradrenolone, fludrocortisone, diflurosone diacetate, fluradrenolone acetonide, medrysone, amcinafel, amcinafide, betamethasone and the balance of it esters, chloroprednisone, chloroprednisone acetate, clorcortelone, clescinolone, dichlorisone, diflurprednate, flucloronide, flunisolide, fluoromethalone, fluperolone, fluprednisolone, hydrocortisone valerate, hyrocortisone cyclopentylpropionate, hydrocortamate meprednisone, paramethasone, prednislone, prednisone, beclomethasone dipropionate, triamcinolone, and mixtures thereof may be used. The preferred steroidal anti-inflammatory for use is hydrocortisone.

A second class of anti-inflammatory agents which is useful in compositions includes the non-steroidal anti-inflammatory agents. The varieties of compounds encompassed by this group are well-known to those skilled in the art. For detailed disclosure of the chemical structure, synthesis, side effects, etc. of non-steroidal anti-inflammatory agents, one may refer to standard texts, including *Antiinflammatory and Anti-Rheumatic Drugs*, K. D. Rainsford, Vol. I-III, CRC Press, Boca Raton, (1985), and *Anti-inflammatory Agents, Chemistry and Pharmacology*, 1, R. A. Scherrer et al., Academic Press, New York (1974).

Specific non-steroidal anti-inflammatory agents useful in the composition invention include, but are not limited to:
1) the oxicams, such as piroxicam, isoxicam, tenoxicam, sudoxicam, and CP-14,304;
2) the salicylates, such aspirin, disalcid, benorylate, trisilate, safapryn, solprin, diflunisal, and fendosal;
3) the acetic acid derivatives, such as diclofenac, fenclofenac, tiopenac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofin, miroprofen, tioxaprofen, suprofen, alminoprofen, and tiaprofenic acid; and
6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the non-steroidal anti-inflammatory agents, ibuprofen, naproxen, flufenamic acid, etofenamate, aspirin, mefenamic acid, meclofenamic acid, piroxicam and felbinac are preferred; ibuprofen, naproxen, ketoprofen, etofenamate, aspirin, and flufenamic acid are more preferred.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol). Manjistha (extracted from plants in genus *Rubia*, particularly *Rubia Cordifolia*), and Guggal (extracted from plants in the genus *Commiphora*, particularly *Commiphora Mukul*), kola extract, chamomile, red clover extract, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$. Specific examples of the foregoing include oil soluble licorice extract, the glycyrrhizic and glycyrrhetic acids themselves, monoammonium glycyrrhetinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

13. Anti-Cellulite Agents

The composition of the present invention may also contain a safe and effective amount of an anti-cellulite agent. Suitable agents may include, but are not limited to, xanthine compounds (e.g., caffeine, theophylline, theobromine, and aminophylline).

14. Topical Anesthetics

The compositions of the present invention may also contain a safe and effective amount of a topical anesthetic. Examples of topical anesthetic drugs include benzocaine, lidocaine, bupivcaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

15. Tanning Additives

The composition of the present invention may contain a tanning active. When present, it is preferable that the compositions contain from about 0.1% to about 20%, more preferably from about 2% to about 7%, and still more preferably from about 3% to about 6%, by weight of the composition, of dihydroxyacetone as an artificial tanning active.

Dihydroxyacetone, which is also known as DHA or 1,3-dihydroxy-2-propanone, is a white to off-white, crystalline powder. This material can be represented by the chemical formula $C_3H_6O_3$ and the following chemical structure:

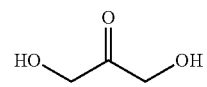

The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See the *Merck Index*, Tenth Edition, entry 3167, p. 463 (1983), and "Dihydroxyacetone for Cosmetics", E. Merck Technical Bulletin, 03-304 110, 319 897, 180 588.

16. Skin Lightening Agents

The compositions of the present invention may contain a skin lightening agent. When used, the compositions preferably contain from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in the World Patent No. WO 1995034280A1 in the name of Hillebrand, Greg G., corresponding to PCT Application No. U.S. Ser. No. 95/07432, filed Jun. 12, 1995; and World Patent No. WO 1995023780A3 in the names of Kvalnes et al., corresponding to PCT Application No. U.S. Ser. No. 95/002809, filed Mar. 1, 1995.

17. Hair Growth Promoters

The compositions of the present invention may contain a hair growth promoter. Hair growth promoters suitable for use herein include minoxidil, procyanidine B-2, prostaglandins, fluridil, ketoconazole, spironolactone, melatonin, and estrogens. A safe and effective amount of a hair growth promoter may be added to the compositions of the present invention, in amounts preferably from about 0.1% to about 30%, more preferably from about 0.5% to about 20%, still more preferably from about 1% to about 5%, by weight of the composition formed.

18. Skin Soothing and Skin Healing Actives

The compositions of the present invention may comprise a skin soothing or skin healing active. Skin soothing or skin healing actives suitable for use herein include panthenoic acid derivatives (including panthenol, dexpanthenol, ethyl panthenol), aloe vera, allantoin, bisabolol, and dipotassium glycyrrhizinate. A safe and effective amount of skin soothing or skin active may be added to the present composition, preferably from about 0.1% to about 30%, more preferably from about 0.5% to about 20%, still more preferably from about 0.5% to about 10%, by weight of the composition formed.

a) Bisabolol

The topical compositions of the present invention may also contain a safe and effective amount of bisabolol. Bisabolol is a naturally occurring unsaturated monocyclic terpene alcohol having the following structure:

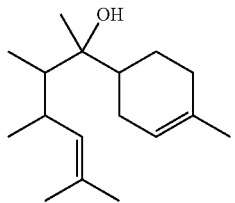 [SMILES: CC(C)=CC(C)C(C)C(C)(O)C1CC=C(C)CC1]

It is the primary active component of chamomile extract/oil. Bisabolol can be synthetic (d,l-alpha-isomer or (+/−)-alpha-isomer) or natural ((−)-alpha-isomer) in origin and can be used as essentially pure compounds or mixtures of compounds (e.g., extracts from natural sources such as chamomile). The alpha form of bisabolol (α-bisabolol) is used in a variety of cosmetic products as a skin conditioning or soothing agent. As used herein, "bisabolol" includes chamomile extract or oil and any isomers and tautomers of such. Suitable bisabolol compounds are commercially available as natural material from Dragoco (Totowa, N.J.) under the product name alpha-bisabolol natural and as a synthetic material from Fluka (Milwaukee, Wis.) under the product name alpha-bisabolol.

In the compositions of the present invention, the composition preferably contains about 0.001% to about 50% by weight of the composition, more preferably from about 0.01% to about 20%, even more preferably from about 0.01% to about 10%, of bisabolol, even more preferably from about 0.1% to about 5%.

19. Antimicrobial and Antifungal Actives

The composition of the present invention may contain an antimicrobial or antifungal active. Such actives are capable of destroying microbes, preventing the development of microbes or preventing the pathogenic action of microbes. A safe and effective amount of an antimicrobial or antifungal active may be added to the present composition, preferably, from about 0.001% to about 10%, more preferably from about 0.01% to about 5%, and still more preferably from about 0.05% to about 2%.

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxypropanol, phenoxyisopropanol, doxycycline, capreomycin, chlorhexidine, chlortetracycline, oxytetracycline, elindamycin, ethambutol, hexamidine, isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythomycin, zinc erythomycin, erythromycin stearate, amikacin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlormeta xylenol, nystatin, tolnaftate, zinc pyrithione, and clotrimazole.

Preferred examples of actives useful herein include those selected from salicylic acid, benzoyl peroxide, 3-hydroxybenzoic acid, glycolic acid, lactic acid, 4-hydroxy benzoic acid, acetyl salicylic acid, 2-hydroxybutanoic acid, 2-hydroxypentanoic acid, 2-hydroxyheanoic acid, cis-retinoic acid, trans-retinoic acid, retinol, phytic acid, N-acetyl-L-cysteine, lipoic acid, azelaic acid, arachidonic acid, benzoyl peroxide, tetracycline, ibuprofen, naproxen, hydrocortisone, acetaminophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

20. Sunscreen Actives

Exposure to ultraviolet light can result in excessive scaling and texture changes of the stratum corneum layer of the epidermis. Therefore, the compositions of the subject invention may optionally contain a sunscreen active. As used herein, "sunscreen active" includes both sunscreen agents and physical sun-blocks. Suitable sunscreen actives may be organic or inorganic.

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens, are present in the amount of from about 0.1% to about 20%, preferably from about 0.5% to about 10%, more preferably from about 1% to about 5%, by weight of the composition.

A wide variety of conventional organic sunscreen actives are suitable for use herein. Sagarin, et al., at Chapter VIII, pages 189 et seq., of *Cosmetics Science and Technology*

(1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexnyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methyl esculetin, daphnetin, and the glucosides, esculin and daphnin); hydrocarbons (diphenylbutadiene, stilbene); dibenzalacetone and benzalacetophenone; naphthosulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane, etocrylene, octocrylene; [3-(4'-methylbenzylideneboman-2-one)], terephthalyidene dicamphor sulfonic acid, and 4-isopropyl-di-benzoylmethane.

Of these, 2-ethylhexyl-p-methoxycinnamate (commercially available as PARSOL MCX), 4,4'-t-butylmethoxydibenzoyl-methane (commercially available as PARSOL 1789), 2-hydroxy-4-methoxybenzophenone, octyldimethyl-p-aminobenzoic acid, digalloytrioleate, 2,2-dihydroxy-4-methoxybenzophenone, ethyl-4-(bis(hydroxy-propyl))aminobenzoate, 2-ethylhexyl-2-cyano-3,-3-diphenylacrylate, 2-ethylhexyl-salicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-aminobenzoate, 2-phenylbenzimidazole-5-sulfonic acid, 2-(p-dimethylaminophenyl)-5-sulfonic-benzoic acid, octocrylene and mixtures of these compounds, are preferred.

More preferred organic sunscreen actives useful in the compositions are 2-ethylhexyl-p-methoxycinnamate, butylmethoxydibenzoylmethane, 2-hydroxy-4-methoxybenzophenone, 2-phenylbenzimidazole-5-sulfonic acid, octyldimethyl-p-aminobenzoic acid, octocrylene, and mixtures thereof.

Also particularly useful in the compositions are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sunscreen agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreen agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid of 2-hydroxy-4-(2-hydroxyehoxy)benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy) dibenzoylmethane and mixtures thereof.

Especially preferred sunscreen actives include 4,4'-t-butylmethoxydibenzoylmethane, 2-ethylhexyl-p-methoxycinnamate, phenyl benzimidazole sulfonic acid, and octocrylene.

A safe and effective amount of the organic sunscreen active is used, typically from about 1% to about 20%, more typically from about 2% to about 10% by weight of the composition. Exact amounts will vary depending upon the sunscreen or sunscreens chosen and the desired Sun Protection Factor (SPF).

21. Particulate Material

The compositions of the present invention may contain a particulate material, preferably a metallic oxide. These particulates can be coated or uncoated, charged or uncharged. Charged particulate materials are disclosed in U.S. Pat. No. 5,997,887 to Ha et al., issued Dec. 7, 1999 and incorporated herein by reference. Particulate materials useful herein include: bismuth oxychloride, iron oxide, mica, mica treated with barium sulfate and titanium dioxide, silica, nylon, polyethylene, talc, styrene, polypropylene, ethylene/acrylic acid copolymer, sericite, aluminum oxide, silicone resin, barium sulfate, calcium carbonate, cellulose acetate, titanium dioxide, polymethyl methacrylate, and mixtures thereof.

Inorganic particulate materials, e.g., $TiO_2$ and $ZrO_2$, are commercially available from a number of sources. One example of a suitable particulate material contains the material available from U.S. Cosmetics (TRONOX $TiO_2$ series, SAT-T CR837, a rutile $TiO_2$). Preferably, particulate materials are present in the composition in levels from about 0.01% to about 2%, more preferably from about 0.05% to about 1.5%, still more preferably from about 0.1% to about 1%, by weight of the composition.

22. Conditioning Agents

The compositions of the present invention may contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to guanidine, urea, glycolic acid and glycolate salts (e.g., ammonium and quaternary alkyl ammonium), salicylic acid, lactic acid and lactate salts (e.g., ammonium and quaternary alkyl ammonium), aloe vera in any of its variety of forms (e.g., aloe vera gel), polyhydroxy alcohols such as sorbitol, mannitol, xylitol, erythritol, glycerol, hexanetriol, butanetriol, propylene glycol, butylene glycol, hexylene glycol and the like, polyethylene glycols, sugars (e.g., melibiose) and starches, sugar and starch derivatives (e.g., alkoxylated glucose, fructose, glucosamine), hyaluronic acid, lactamide monoethanolamine, acetamide monoethanolamine, panthenol, allantoin, and mixtures thereof. Also useful herein are the propoxylated glycerols described in U.S. Pat. No. 4,976,953 to Orr et al., issued Dec. 11, 1990.

Also useful are various $C_1$-$C_{30}$ monoesters and polyesters of sugars related materials. These esters are derived from a sugar or polyol moiety and one or more carboxylic acid moieties. Such ester materials are further described in U.S. Pat. No. 2,831,854 to Martin et al., issued Apr. 22, 1958; U.S. Pat. No. 4,005,196 to Jandacek, issued Jan. 25, 1977; U.S. Pat. No. 4,005,195 to Jandacek, issued Jan. 25, 1977; U.S. Pat. No. 5,306,516 to Letton et al., issued Apr. 26, 1994; U.S. Pat. No. 5,306,515 to Letton et al., issued Apr. 26, 1994; U.S. Pat. No. 5,305,514 to Letton et al., issued Apr. 26, 1994; U.S. Pat. No. 4,797,300 to Jandacek et al., issued Jan. 10, 1989; U.S. Pat. No. 3,963,699 to Rizzi et al., issued Jun. 15, 1976; U.S. Pat. No. 4,518,772 to Volpenhein, issued May 21, 1985, and U.S. Pat. No. 4,517,360 to Volphein, issued May 21, 1985.

Preferably, the conditioning agent is selected from glycerine, propylene glycol, urea, guanidine, sucrose, polyester, panthenol, dexapanthenol, allantoin, and combinations thereof.

23. Structuring Agents

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention contain from about 0.1% to about 20%, more preferably from about 0.1% to about 10%, still more preferably from about 0.5% to about 9% by weight of the composition, of one or more structuring agents.

Preferred structuring agents are those having an HLB of from about 1 to about 8 and having a melting point of at least about 45° C. Suitable structuring agents are those selected from saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with monoglyceride content of at least 40%, $C_{14}$ to $C_{30}$ saturated polyglycerol esters having from about 1 to about 3 alkyl group and from about 2 to 3 saturated glycerol units, $C_{14}$ to $C_{30}$ glycerol monoethers, $C_{14}$ to $C_{30}$ sorbitan mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents of the present invention are selected from stearic acid, palmitic acid, stearyl alcohol, cetyl alcohol, behenyl alcohol, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, and mixtures thereof.

24. Thickening Agents (Including Thickeners and Gelling Agents)

The compositions of the present invention can contain one or more thickening agents, preferably from about 0.1% to about 5%, more preferably from about 0.1% to about 4%, and still more preferably from about 0.25% to about 3%, by weight of the composition.

Non-limiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and of the substituted acrylic acids, wherein the crosslinking agent contains two or more carbon-carbon double bonds and is derived from a polyhydric alcohol. Polymers useful in the present invention are more fully described in U.S. Pat. No. 5,087,445 to Haffey et al., issued Feb. 11, 1992; U.S. Pat. No. 4,509,949 to Huang et al., issued Apr. 5, 1985; U.S. Pat. No. 2,798,053 to Brown, issued Jul. 2, 1957; and in *CTFA International Cosmetic Ingredient Dictionary*, Fourth Edition, 1991, pp. 12 and 80.

Examples of commercially available carboxylic acid polymers useful herein include the carbomers, which are homopolymers of acrylic acid crosslinked with allyl ethers or sucrose or pentaerytritol. The carbomers are available as the Carbopol® 900 series from B.F. Goodrich (e.g., Carbopol® 954). In addition, other suitable carboxylic acid polymeric agents include copolymers of $C_{10\text{-}30}$ alkyl acrylates with one or more monomers of acrylic acid, methacrylic acid, or one of their short chain (i.e., $C_{1\text{-}4}$ alcohol) esters, wherein the crosslinking agent is an allyl ether of sucrose or pentaetytritol. These copolymers are known as acrylates/$C_{10\text{-}30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/$C_{10\text{-}30}$ alkyl acrylate crosspolymers, and mixtures thereof.

b) Crosslinked Polyacrylate Polymers

The compositions in the present invention can optionally contain crosslinked polyacrylate polymers useful as thickening or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660 to Hawe et al., issued Mar. 31, 1992; U.S. Pat. No. 4,849,484 to Heard, issued Jul. 18, 1989; U.S. Pat. No. 4,835,206 to Farrar et al., issued May 30, 1989; U.S. Pat. No. 4,628,078 to Glover et al., issued Dec. 9, 1986; U.S. Pat. No. 4,599,379 to Flesher et al., issued Jul. 8, 1986; and EP 228, 868 to Farrar et al., published Jul. 15, 1987.

c) Polyacrylamide Polymers

The compositions of the present invention can optionally contain polyacrylamide polymers, especially nonionic polyacrylamide polymers including substituted, branched, or unbranched polymers. More preferred among these polyacrylamide is the nonionic polymer given the CTFA designation polyacrylamide and isoparaffin and laureth-7, available under the trade name Sepigel 305 from Seppic Corporation (Fairfield, N.J.).

Other polyacrylamide polymers useful herein include multi-block copolymers of acrylamides and substituted acrylamides, with acrylic acids and substituted acrylic acids. Commercially available examples of these multi-block copolymers include Hypan SR150H, SS500V, SS500W, SSSA100H from Lipo Chemicals, Inc. (Patterson, N.J.).

d) Polysaccharides

A wide variety of polysaccharides are useful herein. "Polysaccharides" refer to gelling agents which contain a backbone of repeating sugar (i.e., carbohydrate) units. Non-limiting examples of polysaccharide gelling agents include those selected from cellulose, carboxymethylhydroxyethylcellulose, cellulose acetate propionate carboxylate, hydroxyethylcellulose, hydroxyethylethylcellulose, hydroxypropylcellulose, hydroxypropylmethylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxylated (preferably hydroxyethylated or hydroxypropylated) to form a hydroxylated cellulose which is then further modified with a $C_{10}$-$C_{30}$ straight chain or branched chain alkyl group through an ether linkage. Typically, these polymers are ethers of $C_{10}$-$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e., alkyl groups derived from the alcohols of coconut oil), palmityl, oleyl, linoeyl, linolenyl, ricinoleyl, behenyl, and mixtures thereof. Preferred among the alkyl hydroxyalkyl cellulose ethers is the material given the CFTA designation cetyl hydroxyethylcellulose, which is the ether of cetyl alcohol and hydroxyethylcellulose. This material is sold under the trade name Natrosol® CS Plus from Aqualon Corporation (Wilmington, Del.).

Other useful polysaccharides include scleroglucans which are a linear chain of (1-3) linked glucose units with a (1-6) linked glucose every three units, a commercially available example of which is Clearogel™ CS11 from Michel Mercier Products Inc. (Mountainside, N.J.).

e) Gums

Other thickening and gelling agent useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

25. Aquaporin Stimulators

The compositions of the present invention may contain a safe and effective amount of an aquaporin stimulator. Aquaporin stimulators are particularly useful for maintaining optimal hydration levels in the skin as described in U.S. application Ser. No. 12/297,734, filed Mar. 28, 2007 (corresponding to PCT No. PCT/EP07/52978). Non-limiting examples of aquaporin stimulators suitable for use in the compositions of the present invention include glycerol glycosides, in particular hexosyl glycerides and/or (hexosyl) hexosyl glycerides; cAMP analogs; PKA-(adenylyl cyclase) activators; and phosphodiesterase inhibitors, in particular caffeine and theophylline.

In the compositions of the present invention, the aquaporin stimulator preferably is included in an amount from about 0.0001% to about 20%, more preferably from about 0.0005% to about 10%, and still more preferably from about 0.001% to about 5%, by weight of the composition.

Another embodiment of the present invention relates to cosmetic compositions containing N-M-A-N-A-K (SEQ ID NO: 1), an NF-κB-inhibitor. In some embodiments a combination of other actives known to clear up inflammation, normalize the skin tissues. An NF-κB-inhibitor may have difficulty working quickly and efficiently when inflammation is manifested in the skin. The strategy adopted, is to use a specific heptapeptide that functions as a TGF-β1 mimic. Activating TGF-β receptors starts the anti-inflammatory cascade as many things are upregulated which are responsible for tissue normalization; simplistically, collagen is upregulated and metalloproteinases are downregulated. Testing has established that a TGF-β1 mimic, heptapeptide, A-N-V-A-E-N-A (SEQ ID NO: 2), not only has the ability to promote tissue repair and to reduce inflammation but also to enhance the moisture content of the skin by upregulating aquaporins. The effectiveness of N-M-A-N-A-K (SEQ ID NO: 1) at downregulating the release of NF-κB is enhanced, and the skin is rapidly restored to a normal healthy condition with a youthful appearance.

Cosmetic preparations for topical application are formulated to be practically sterile; this is normally achieved by incorporating preservatives, which have antimicrobial function. N-M-A-N-A-K (SEQ ID NO: 1) is not biologically active in itself, but has the ability—due to its electronic configuration and molecular shape—to bind to the cell's signaling antennae involved in regulation of the inflammatory cascade. It has been reported that biological actives developed for skin care are often de-activated by the preservatives used. In the case of peptides, such as N-M-A-N-A-K (SEQ ID NO: 1), this is not a concern.

The hexapeptide, N-M-A-N-A-K (SEQ ID NO: 1), which functions as an NF-κB-inhibitor can be used with cosmetically acceptable acids and bases to form "salts" and still retain its cosmetic effectiveness when modulating age-related effects. Examples of organic and inorganic acids include: hydrochloric, phosphoric, acetic, benzoic, citric, salicylic, malic, fumaric, succinct, lactic, gluconic, ascorbic, etc. Examples of organic bases include: methyl amine, triethanolamine, amino acids such as lysine, guanidine, glutamine and arginine, aminomethylpropanol, and the like.

Numerous vehicles for topical application of cosmetic compositions are known in the art. See, e.g. Remington's Pharmaceutical Sciences, Gennaro A R, ed., 20th Edition, 2000. All compositions usually employed for topically administering cosmetic compositions, e.g., creams, lotions, gels, dressings, shampoos, tinctures, pastes, ointments, salves, powders, liquid or semi-liquid formulation, patches, liposomal preparations and the like, may be used. Application of said compositions may, if appropriate, be by aerosol with a propellant such as nitrogen, a pump-spray, etc. If needed, the N-M-A-N-A-K (SEQ ID NO: 1) can be pre-dissolved in an appropriate solvent, such as ethanol or glycerine, before dispersion in the vehicle; however, this is not required. The main fact here is that the NF-κB-inhibitor, N-M-A-N-A-K (SEQ ID NO: 1) is "non-reactive" with most cosmetic ingredients and will maintain its ability to suppress NF-κB formation, returning it to the normal levels reflected in youthful normal skin.

The NF-κB-inhibitor N-M-A-N-A-K (SEQ ID NO: 1) has been formulated in cosmetic lotions and creams for human use studies.

(B) Dermatologically Acceptable Carriers

The topical compositions of the present invention also contain a dermatologically acceptable carrier. The phrase "dermatologically acceptable carrier," as used herein, means that the carrier is suitable for topical application to the epidermal layer of the skin, has good aesthetic properties, is compatible with the actives of the present invention and any other components, and will not cause any untoward safety or toxicity concerns. A safe and effective amount of carrier is from about 50% to about 99.99%, preferably from about 80% to about 99.99%, more preferably from about 90% to about 98%, and even more preferably from about 90% to about 95% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers contain an emulsion such as oil-in-water emulsions, water-in-oil emulsions, and water-in-silicone emulsions. As will be understood by the skilled artisan, a given component will distribute primarily into either the water or oil/silicone phase, depending on the water solubility/dispersibility of the component in the composition. Oil-in-water emulsions are especially preferred.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic, or cationic. Suitable emulsifiers are disclosed in, for example, U.S. Pat. No. 3,755,560 to Dickert et al., issued Aug. 28, 1973; U.S. Pat. No. 4,421,769 to Dixon et al., issued Dec. 20, 1983; and McCutcheon's Detergents and Emulsifiers, North American Addition, pages 317-324 (1986).

The emulsion may also contain an anti-foaming agent to minimize foaming upon application to the epidermal layer. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, still more preferably 5 centistokes or less.

Preferred water-in-silicone and oil-in-water emulsions are described in greater detail below:

1. Water-in-Silicone Emulsion

Water-in-silicone emulsions contain a continuous silicone phase and a dispersed aqueous phase.

a) Continuous Silicone Phase

Preferred water-in-silicone emulsions of the present invention contain from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for a retinoid. The continuous silicone phase of the preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase. These preferred emulsion systems provide more oxidative stability to the retinoid over extended periods of time than comparable water-in-oil emulsions containing lower concentrations of the polyorganosiloxane oil. Concentrations of non-silicone oils in the continuous silicone phase are minimized or avoided altogether so as to further enhance the oxidative stability of the selected retinoid in the composition. Water-in-silicone emulsions of this type are described in World Patent No. WO 1997021423A1 in the names of Hillebrand et al., corresponding to PCT Application No. U.S. Ser. No. 96/019302, filed Dec. 4, 1996.

The polyorganosiloxane oil for use in the composition may be volatile, non-volatile, or a mixture of volatile and non-volatile silicones. The term "non-volatile" as used in the context refers to those silicones that are liquid under ambient conditions and have a flash point (less than one atmosphere of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having one to about 30 carbon atoms (preferably R is methyl or ethyl, more preferably methyl; also mixed alkyl groups can used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is a straight or branched chain alkyl having from about 2 to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and still more preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e., n=4), Dow Corning® 344 fluid having a viscosity of 2.5 centistokes and a boiling point of 178° C., which primarily contains the cyclomethicone pentamer (i.e., n=5), Dow Corning® 245 fluid having a viscosity of 4.2 centistokes and a boiling point of 205° C., which primarily contains a mixture of the cyclomethicone tetramer and pentamer (i.e., n=4 and 5), and Dow Corning® 345 fluid having a viscosity of 4.5 centistokes and a boiling point of 217° C., which primarily contains a mixture of the cyclomethicone tetramer, pentamer, and hexamer (i.e., n=4, 5, and 6).

Also useful are materials such as trimethylsiloxysilicate, which is a polymeric material corresponding to the general chemical formula $[(CH_2)_3SiO_{1/2}]_x[SiO_2]_y$, wherein X is an integer from about 1 to about 550 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$, wherein R is an alkyl group (preferably R is methyl or ethyl, more preferably methyl) and n is an integer from about 0 to about 500, chosen to achieve the desired molecular weight. Commercially available dimethiconols are typically sold as mixtures with dimethicone or cyclomethicone (e.g., Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from polyalkylsiloxanes, alkyl substituted dimethicones, cyclomethicones, trimethylsiloxysilicated, dimethiconols, polyalkylaryl siloxanes, and mixtures thereof. More preferably for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of the selected retinoid in the composition. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semi-synthetic oils etc.

b) Dispersed Aqueous Phase

The topical compositions of the present invention contain from about 30% to about 90%, more preferably from about 50% to about 85%, and still more preferably from about 70% to about 80% of a dispersed aqueous phase. In emulsion technology, the term "dispersed phase" is a term well-known to one skilled in the art, which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in or surrounded by the continuous silicone phase described hereinbefore.

The aqueous phase can be water or a combination of water and one or more water soluble or dispersible ingredients. Non-limiting examples of such ingredients thickeners, acids, bases, salts, chelants, gums, water-soluble or dispersible alcohols and polyols, buffers preservatives, sunscreen agents, colorings, and the like.

The topical compositions of the present invention will typically contain from about 25% to about 90%, preferably from about 40% to about 80%, more preferably from about 60% to about 80%, water in the dispersed aqueous phase by weight of the composition.

c) Emulsifier for Dispersing the Aqueous Phase

The water-in-silicone emulsions of the present invention preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present invention, and provides the desired dispersion characteristics. Suitable emulsifiers include silicone emulsifiers, non-silicone-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having a HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also know to those skilled in the art as silicone surfactants. Useful silicone emulsifiers include dimethicone copolyols. These materials are polydiemthylsiloxanes which have been modified to include polyether side-chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain $C_2$-$C_{30}$ pendant side-chains. Still other useful dimethicone copolyols include materials having various cationic, anionic, amphoteric, and zwitterionic pendant moieties.

The dimethicone copolyol emulsifiers useful herein can be described by the following general structure:

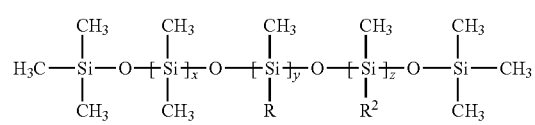

wherein R is $C_1$-$C_{30}$ straight, branched, or cyclic alkyl and $R^2$ is selected from the group consisting of

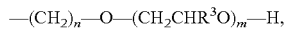

and

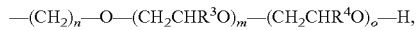

wherein n is an integer from 3 to about 10; $R^3$ and $R^4$ are selected from the group consisting of H and $C_1$-$C_6$ straight or branched chain alkyl such that $R_3$ and $R_4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

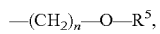

wherein $R^5$ is a cationic, anionic, amphoteric, or zwitterionic moiety.

Non-limiting examples of the dimethicone copolyols and other silicone surfactants useful as emulsifiers herein include polydimethylsiloxane polyether copolymers with pendant polyethylene oxide side-chains, polydimethylsiloxane polyether copolymers with pendant polypropylene oxide side-chains, polydimethylsiloxane polyether copolymers with pendant mixed polyethylene oxide and polypropylene oxide side-chains, polydimethylsiloxane polyether copolymers with pendant mixed poly(ethylene)(polypropylene) oxide side-chains, polydimethylsiloxane polyether copolymers with pendant organobetaine side-chains, polydimethylsiloxane polyether copolymers with pendant carboxylate side-chains, polydimethylsiloxane polyether copolymers with pendant quaternary ammonium side-chains; and also further modifications of the preceding copolymers containing pendant $C_2$-$C_{30}$ straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the trade name ABIL® WE-09 (available from Goldschmidt). Cetyl dimethicone copolyol is also commercially available as a mixture with hexyl laurate (and) polyglyceryl-3 oleate (and) cetyl dimethicone and is sold under the trade name ABIL® WS-08 (also available from Goldschmidt). Other non-limiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol methyl ether, dimethicone copolyol phosphate, and dimethicone copolyol stearate. See *International Cosmetic Ingredient Dictionary*, Fifth Edition, 1993.

Dimethicone copolyol emulsifiers useful herein are described for example in U.S. Pat. No. 4,960,764 to Figueroa, Jr. et al., issued Oct. 2, 1990; European Pat. No. EP 330,369 to SanoGueira, published Aug. 30, 1989; G. H. Dahms et al., "New Formulation Possibilities Offered by Silicone Copolyols," *Cosmetics & Toiletries*, vol. 110, pp. 91-100, March 1995; M. E. Carlotti et al., "Optimization of W/O—S Emulsions and Study of the Quantitative Relationships between Ester Structure and Emulsion Properties," *J. Dispersion Science and Technology*, 13(3), 315-336 (1992); P. Hameyer, "Comparative Technological Investigations of Organic and Organosilicone Emulsifiers in Cosmetic Water-in-Oil Emulsion Preparations," HAPPI 28(4), pp. 88-128 (1991); J. Smid-Korber et al., "Efficiency and usability of silicone surfactants in emulsions," *Provisional Communication International Journal of Cosmetic Science*, 12, 135-139 (1990); and D. G. Krzysik et al., "A New Silicone Emulsifier for Water-in-Oil Systems," *Drug and Cosmetic Industry*, vol. 146(4) pp. 28-81 (April 1990).

Among the non-silicone-containing emulsifiers useful herein are various non-ionic and anionic emulsifying agents such as sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued De. 30, 1983; and U.S. Pat. No. 3,755,560 to Dickert et al., issued Aug. 28, 1973.

Non-limiting examples of these non-silicone-containing emulsifiers include: polyethylene glycol 20 sorbitan monolaurate (Polysorbate 2), polyethylene glucol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, Ceteth-10, diethanolamine cetyl phosphate, glyceryl stearate, PEG-100 stearate, and mixtures thereof.

2. Oil-in-Water Emulsions

Other preferred topical carriers include oil-in-water emulsions, having a continuous aqueous phase and a hydrophobic, water-insoluble phase ("oil phase") dispersed therein. Examples of suitable oil-in-water emulsion carriers are described in U.S. Pat. No. 5,073,371 to Turner, D. J. et al., issued Dec. 17, 1991, and U.S. Pat. No. 5,073,372 to Turner, D. J. et al., issued De. 17, 1991. An especially preferred oil-in-water emulsion, containing a structuring agent, hydrophilic surfactant, and water is described in detail hereinafter.

a) Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the compound. The structuring agent may also function as an emulsifier or surfactant. Preferred compositions of this invention contain from about 0.5% to about 20%, more preferably from about 1% to about 10%, even more preferably from about 1% to about 5%, by weight of the composition, of a structuring agent.

The preferred structuring agents of the present invention include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

b) Hydrophilic Surfactant

The preferred oil-in-water emulsions contain from about 0.05% to about 10%, preferably from about 1% to about 6%, and more preferably from about 1% to 3% of at least one hydrophilic surfactant, which can disperse the hydrophobic materials in the water phase (percentages by weight of the topical carrier). The surfactant, at a minimum, must be hydrophilic enough to disperse in water.

Preferred hydrophilic surfactants are selected from non-ionic surfactants. Among those nonionic surfactants that are useful herein are those that can be broadly defined as condensation products of long chain alcohols, e.g., $C_8$-$C_{30}$ alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1,000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_8$-$C_{20}$ alkyl group, and n is an integer from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e., alkylene oxide esters of fatty acids). These materials have the general formula $RCO(X)_n OH$ wherein R is a $C_{10}$-$C_{30}$ alkyl group, X is —$OCH_2CH_2$— (i.e., derived from ethylene glycol or oxide) or —$CH_2CH_2CH_3$— (i.e., derived from propylene glycol or oxide), and n is an integer from about 6 to about 200. Other nonionic surfactants are the condensation products of alkylene oxides with 2 moles of fatty acids (i.e., alkylene oxide diesters of fatty acids). These materials have the general formula $RCO(X)_n OOCR$ wherein R is a $C_{10}$-$C_{30}$ alkyl group, X is —$OCH_2CH_2$— (i.e., derived from ethylene glycol or oxide) or —$CH_2CH_2CH_3$— (i.e., derived from propylene glycol or oxide), and n is an integer from about 6 to about 100. Other nonionic surfactants are the condensation products of alkylene oxides with fatty alcohols (i.e., alkylene oxide ethers of fatty alcohols). These materials have the general formula $R(X)_n OR'$ wherein R is a $C_{10}$-$C_{30}$ alkyl group, X is —$OCH_2CH_2$— (i.e., derived from ethylene glycol or oxide) or —$CH_2CH_2CH_3$— (i.e., derived from propylene glycol or oxide), and n is an integer from about 6 to about 100 and R' is H or a $C_{10}$-$C_{30}$ alkyl group. Still other nonionic surfactants are the condensation products of alkylene oxides with both fatty acids and fatty alcohols [i.e., wherein the polyalkylene oxide portion is esterified on one end with a fatty acid and etherified (i.e., connected via an ether linkage) on the other end with a fatty alcohol]. These materials have the general formula $RCO(X)_n OR'$ wherein R and R' are $C_{10}$-$C_{30}$ alkyl groups, X is —$OCH_2CH_2$— (i.e., derived from ethylene glycol or oxide) or —$CH_2CH_2CH_3$— (i.e., derived from propylene glycol or oxide), and n is an integer from about 6 to about 100. Non-limiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

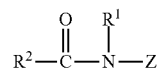

wherein $R^1$ is H, $C_1$-$C_4$ alkyl, 2-hydroxyethyl, 2-hydroxypropyl, preferably $C_3$-$C_4$ alkyl, more preferably methyl or ethyl, most preferably methyl; $R^2$ is $C_5$-$C_{31}$ alkyl or alkenyl, preferably $C_7$-$C_{19}$ alkyl or alkenyl, more preferably $C_9$-$C_{17}$ alkyl or alkenyl, most preferably $C_{11}$-$C_{15}$ alkyl or alkenyl; and Z is a polyhydroxyhydrocarbyl moiety having a linear hydrocarbyl chain with at least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methylglucoside amide (i.e., wherein the $R^2CO$— moiety is derived from coconut fatty acids). Processes for making compositions containing polyhydroxy fatty acid amides are disclosed, for example, in G. B. Patent Specifications 809,060, published Feb. 18, 1959 by Thomas Hedley & Co., Ltd.; U.S. Pat. No. 2,965,576 to Wilson, E. R., issued Dec. 20, 1960; U.S. Pat. No. 2,703,798 to Schwartz, A. M., issued Mar. 8, 1955; and U.S. Pat. No. 1,985,424 to Piggott, issued Dec. 25, 1934; which are incorporated herein by reference in their entirety.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, and mixtures thereof. Non-limiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate-80, cetyl phosphate, potassium cetyl phosphate, diethanolamine cetyl phosphate, Polysorbate-60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, PEG-100 stearate, and mixtures thereof.

Another group of nonionic surfactants useful herein are fatty acid ester blends based on a mixture of sorbitan or sorbitol fatty acid ester and sucrose fatty acid ester, the fatty acid in each instance being preferably $C_8$-$C_{24}$, more preferably $C_{10}$-$C_{20}$. The preferred fatty acid ester emulsifier is a blend of sorbitan or sorbitol $C_{16}$-$C_{20}$ fatty acid ester with sucrose $C_{10}$-$C_{16}$ fatty acid ester, especially sorbitan stearate and sucrose cocoate. This is commercially available from ICI under the trade name Arlatone 2121.

Other suitable surfactants useful herein include a wide variety of cationic, anionic, zwitterionic, and amphoteric surfactants such as are known in the art and discussed more fully below. See, e.g., McCutcheon's, *Detergents and Emulsifiers*, North American Edition (1986), published by Allured Publishing Corporation; U.S. Pat. No. 5,011,681 to Ciotii et al., issued Apr. 30, 1991; U.S. Pat. No. 4,412,769 to Dixon et al., issued Dec. 20, 1983; and U.S. Pat. No. 3,755,560 to Dickert et al., issued Aug. 28, 1973; these four (4) references are incorporated herein by reference in their entirety. The hydrophilic surfactants useful herein can contain a single surfactant or any combination of suitable surfactants. The exact surfactant (or surfactants) chosen will depend upon the pH of the composition and the other components present.

Also useful herein are cationic surfactants, especially dialkyl quaternary ammonium compounds, examples of which are described in U.S. Pat. No. 5,151,209; U.S. Pat. No. 5,515,210; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's *Detergents and Emulsifiers*, North American Edition, M. C. Publishing Co. (1989); and Schwartz et al., *Surface Active Agents, Their Chemistry and Technology*, New York: Interscience Publishers, (1949); which descriptions are incorporated herein by reference. The cationic surfactants useful herein include cationic ammonium salts such as those having the formula:

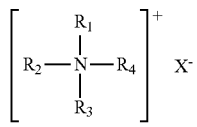

wherein $R_1$ is an alkyl group having from about 12 to about 30 carbon atoms, or an aromatic, aryl, or alkaryl group having from about 12 to about 30 carbon atoms; $R_2$, $R_3$, and $R_4$ are independently selected from hydrogen, an alkyl group having from about 1 to 22 carbon atoms, or aromatic, aryl, or alkaryl groups having from about 12 to about 22 carbon atoms; and X is any compatible anion, preferably selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain an ester and/or ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 about 3 carbon atoms; and X is as described previously.

Still more preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is instead $R_5CONH-(CH_2)_n$, wherein $R_5$ is an alkyl group having from about 12 to about 22 carbon atoms, and n is an integer from about 2 to about 6, more preferably from about 2 to about 4, and still more preferably from about 2 to about 3. Non-limiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Non-limiting examples of quaternary ammonium salt cationic surfactants include those selected from cetyl ammoniumchloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG-dimonium chloride, dilauryl dimethyl ammonium chloride, distearyl dimethyl ammonium chloride, dimyristyl dimethyl ammonium chloride, dipalmityl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl diethyl ammonium chloride, stearamidopropyl dimethyl ammonium lactate, and mixtures thereof.

Still more preferred cationic surfactants are those selected from behenamidopropyl PG-dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactants and structuring agent is behenamidopropyl PG-dimonium chloride and/or behenyl alcohol, wherein the ratio is preferably optimized to maintain and to enhance physical and chemical stability, especially when such a combination contains ionic and/or highly polar solvents. This combination is especially useful for delivery of sunscreen agents such as zinc oxide and octyl methoxycinnamate.

A wide variety of anionic surfactants are also useful herein. See, e.g., U.S. Pat. No. 3,929,678 to Laughlin et al., issued Dec. 30, 1975, which is incorporated herein by reference in its entirety. Non-limiting examples of anionic surfactants include the alkyl isethionates and the alkyl and alkyl ether sulfates. The alkyl isethionates typically have the formula $RCO-OCH_2CH_2SO_3M$ wherein R is alkyl or alkenyl of from about 10 to about 30 carbon atoms, and M is a water-soluble cation such as ammonium, sodium, potassium, or triethanolamine. Non-limiting examples of these isethionates include those alkyl isethionates selected from ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium, or triethanolamine. Another suitable class of anionic surfactants are the water-soluble salts of the organic, sulfuric acid reaction products of the general formula:

$$R-SO_3\text{-}M$$

wherein R is chosen from the group including a straight or branched chain, saturated aliphatic hydrocarbon radical having from about 8 to about 24, preferably from about 10 to about 16 carbon atoms; and M is a cation. Still other anionic synthetic surfactants include the class designated as succinamates, olefin sulfonates having about 12 to about 24 carbon atoms, and β-alkoxy alkane sulfonates. Examples of these materials are sodium lauryl sulfate and ammonium lauryl sulfate.

Other anionic materials useful herein are soaps (i.e., alkali metal salts, e.g., sodium or potassium salts) of fatty acids typically having from about 8 to about 24 carbon atoms, preferably from about 10 to about 20 carbon atoms. The fatty acids used in making soap can be obtained from natural sources such as, for instance, plant or animal derived glycerides (e.g., palm oil, coconut oil, soybean oil, castor oil, tallow, lard, etc.). The fatty acids can also be synthetically prepared. Soaps are described in more detail in U.S. Pat. No. 4,557,853 to Collins, issued Dec. 10, 1985.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[(CH_2)_mCO_2M]_2$ and $RNH(CH_2)_mCO_2M$ wherein m is from 1 to 4, R is a $C_8$-$C_{22}$ alkyl or alkenyl, and M is H, alkali metal, alkaline earth metal, ammonium, or alkanolammonium. Also included are imidazolinium and ammonium derivatives. Specific examples of suitable amphoteric surfactants include sodium 3-dodecyl-amino proprionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as cocamidopropyl PG-dimonium chloride phosphate (commercially available as Monaquat PTC, from Mona Corp.).

Other amphoteric or zwitterionic surfactants useful herein include betaines. Examples of betaines include the higher alkyl betaines, such as coco dimethyl carboxymethyl betaine, lauryl dimethyl carboxymethyl betaine, lauryl dimethyl alphacarboyethyl betaine, cetyl dimethyl carboxymethyl betaine, cetyl dimethyl betaine (available as Lonzaine 16SP from Lonza Corp.), lauryl bis-(2-hydroxylethyl) carboxymethyl betaine, stearyl bis-(2-hydroxpropyl) carboxymethyl betaine, oleyl dimethyl gamma-carboxypropyl betaine, lauryl bis-(2-hydroxypropyl) alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkonyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

c) Water

The preferred oil-in-water emulsion contains from about 25% to about 98%, preferably from about 65% to about 95%, more preferably from about 10% to about 90% water by weight of the topical carrier.

The hydrophobic phase is dispersed in the continuous aqueous phase. The hydrophobic phase may contain water insoluble or partially insoluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may contain a dermatologically acceptable emollient. Such compositions preferably contain from about 1% to about 50% of the emollient. As used herein, "emollient" refers to a material useful for the prevention of relief of dryness, as well as for the protection of the skin. Wide varieties of suitable emollients are known and may be used herein. Sagarin's, *Cosmetics Science and Technology*, 2nd Edition, vol. 1, pp. 32-43 (1972), incorporated herein by reference, contains numerous examples of materials suitable as an emollient. A preferred emollient is glycerin. Glycerin is preferably used in an amount from or about 0.001% to about 30%, more preferably from or about 0.01% to about 20%, still more preferably from or about 0.1% to about 10%, e.g., 5%.

Lotions and creams according to the present invention generally contain a solution carrier system and one or more emollients. Lotions and creams typically contain from about 1% to about 50%, preferably from about 1% to about 20%, of emollient, from about 50% to about 90%, preferably from about 60% to about 80%, water; and the TGF-β mimic and/or TGF-β mimic derivative and the additional skin care active (or active) in the above described amounts. Creams are generally thicker than lotions due to high levels of emollients or higher levels of thickeners.

Ointments in the present invention may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin's, *Cosmetic Science and Technology*, 2nd Edition, Vol. 1, pp. 72-73 (1972), incorporated herein by reference, and/or an emollient. For example, an ointment may contain from about 2% to about 10% of an emollient; from about 0.1% to about 2% of a thickening agent; and the TGF-β mimic and/or the TGF-β mimic derivative and the additional skin care active (or actives) in the above described amounts.

Compositions of this invention useful for cleansing ("cleansers") are formulated with a suitable carrier, e.g., as described above, and preferably contain, in addition to the TGF-β mimic and/or TGF-β mimic derivative and the additional skin care active (or actives) in the above described amounts, from about 1% to about 90%, more preferably from about 5% to about 10%, of a dermatologically acceptable surfactant. The surfactant is suitably selected from anionic, nonionic, zwitterionic, amphoteric, and ampholytic surfactants, as well as mixtures of these surfactants. Such surfactants are well known to those skilled in the detergency art. Non-limiting examples of possible surfactants include isoceteth-20, sodium methyl cocoyl taurate, sodium methyl oleoyl taurate, and sodium lauryl sulfate. See U.S. Pat. No. 4,800,197 to Kowcz et al., issued Jan. 24, 1989, which is incorporated herein by reference in its entirety, for exemplary surfactants useful herein. Examples of a broad variety of additional surfactants useful herein are described in McCutcheon's, *Detergents and Emulsifiers*, North American Edition (1986), published by Allured Publishing Corporation. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, and mousses. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148 to Barford et al., issued May 30, 1989.

A used herein, the term "foundation" refers to a liquid, semi-liquid, semi-solid, or solid skin cosmetic which includes, but is not limited to lotions, creams, gels, pastes, cakes, and the like. Typically, the foundation is used over a large area of the skin, such as over the face, to provide a particular look. Foundations are typically used to provide an adherent base for color cosmetics such as rouge, blush, powder and the like, and tend to hide skin imperfections and impart a smooth, even appearance to the skin. Foundations of the present invention include a dermatologically carrier and may include conventional ingredients such as oils, colorants, pigments, emollients, fragrances, waxes, stabilizers, and the like. Exemplary carriers and such other ingredients which are suitable for use herein are described, for example, in World Patent No. WO 1996033689A1 in the names of Barford et al., corresponding to PCT Application No. U.S. Ser. No. 96/004302, filed Mar. 29, 1996.

VI. Composition Preparation

The compositions of the present invention are generally prepared by conventional methods such as are known on the art of making topical compositions. Such methods typically involve mixing of the ingredients in one or more steps to a relatively uniform state, with or without heating, cooling, under reduced pressures, and the like.

VII. Methods for Managing Skin Condition

The compositions of the present invention are useful for managing and optimizing mammalian skin health by way of both prophylactic and therapeutic means. For example, methods are directed to thickening various skin layers (i.e., epidermis or dermis); preventing the thinning of the skin; preventing and/or retarding the appearance of spider vessels and/or red blotchiness of the skin; preventing and/or retarding the appearance of dark circles under the eyes; preventing and/or retarding sallowness of the skin; improving firmness and elasticity of the skin; softening and/or smoothing lips, hair and nails; preventing and/or relieving itch; preventing and/or eliminating wrinkles and fine lines; stimulating collagen synthesis; reducing recovery time following chemical peels, and stimulating natural hydration of the skin.

The method of improving skin appearance involves topically applying to the skin an effective amount of the composition of the present invention. The amount of the composition required, the frequency of the application, and the duration of use will depend on the amount of TGF-β mimic, analogs, or derivatives thereof contained in the composition as well as on the specific combination with the other ingredients in the composition and on the level of effect desired.

Ideally, the composition is applied regularly to the skin. "Regularly," as used herein, means over an extended period of time during the subject's lifetime, preferably for a period of at least one week, more preferably for a period of at least about one month, even more preferably for at least about three months, even more preferably for at least about six months, and more preferably still for at least about one year.

While benefits will be realized after various periods of use (e.g., weeks, months, years), due to the prophylactic properties of the present invention, it is preferred that regular applications continue throughout the subject's lifetime. Typically, applications would be on the order of about once a day over such extended periods, however, application rates can vary from about once per week up to about three times per day or more as needed.

Amounts of the composition and products applied to the skin are, per application, preferably in the range of from about 0.1 mg/cm$^2$ to about 10 mg/cm$^2$. A particularly useful application amount is about 1 mg/cm$^2$ to about 2 mg/cm$^2$.

The method of managing optimal skin health with the present invention is preferably practiced by, but not limited to, applying the composition in the form of a skin lotion, cream, gel, foam, ointment, paste, emulsion, spray, conditioner, tonic, cosmetic make-up, lipstick, foundation, aftershave, and the like, to the skin and allowing the composition to remain there. The composition can be applied manually, with the aid of spatulas, wipes, or similar cosmetic tools. It can also be applied by the use of an occlusive or semi-occlusive patch, as well as with an adhesive or non-adhesive tissue.

EXAMPLES

The following examples are provided to further describe and demonstrate embodiments within the scope of the present invention. The examples are given solely for the purpose of illustration and are not to be construed as limitations of the present invention, as many variations thereof are possible without departing from the spirit and scope of the invention.

TABLE 2

Cosmetic Lotion

| Components | Quantity |
| --- | --- |
| Water - deionized or distilled | qs. to 100% |
| Trimethylolpropane Tricaprylate/Tricaprate | 10.0% |
| Glycerin | 2.0% |
| Cetearyl Alcohol | 1.0% |
| Ceteareth-20 | 1.0% |
| Glyceryl Stearate | 1.0% |
| Steareth-2 | 0.5% |
| Ceteth 24 | 0.2% |
| Choleth-24 | 0.2% |
| PEG-100 Stearate | 0.1% |
| Phospholipids | 0.1% |
| Arginine | 0.3% |
| Dimethicone | 0.5% |
| Ammonium Acryloyldimethyl-taurate/ VP Copolymer | 1.0% |
| Salicylic Acid | 0.2% |
| Phenoxyethanol | 1.0% |
| N-M-A-N-A-K (SEQ ID NO: 1) | 0.0001% |

Procedure: Heat the oils and emulsifiers to 70° C. Heat the water plus glycerine, salicylic acid and arginine to 60° C. Mix together and cool to 45° C. Add the N-M-A-N-A-K (SEQ ID NO: 1) and the phenoxyethanol. Homogenize. Add the thickener and mix until a uniform viscous product results.
Specifications: pH 6.0, viscosity 80,000 cps.

TABLE 3

Cosmetic Cream

| Components | Quantity |
| --- | --- |
| Water - deionized or distilled | qs. to 100% |
| Hydresia - Safflower Oleosomes | 15.0% |

TABLE 3-continued

Cosmetic Cream

| Components | Quantity |
| --- | --- |
| Dimethicone | 1.0% |
| Arginine | 0.6% |
| Salicylic Acid | 0.5% |
| Superoxide Dismutase | 0.1% |
| Niacin | 0.1% |
| Mixed tocopherols | 0.05% |
| Retinol Palmitate | 0.1% |
| A-N-V-A-E-N-A (SEQ ID NO: 2) | 0.0001% |
| Glycerin | 2.0% |
| Xanthan Gum | 0.8% |
| Tragacanth Gum | 0.5% |
| Phenoxyethanol | 1.0% |
| N-M-A-N-A-K (SEQ ID NO: 1) | 0.0001% |

Procedure: The water soluble ingredients, arginine, salicylic acid, superoxide dismutase, Niacin, A-N-V-A-E-N-A (SEQ ID NO: 2), and N-M-A-N-A-K (SEQ ID NO: 1) are mixed together at 25° C. The two gums are dispersed in the glycerin and added to the water solution. The Hydresia is added to the aqueous phase along with the oily actives, Vitamin A, Vitamin E. The emulsion is stirred until a thick uniform cream is obtained.
Note:
This is a cold process.
Specifications: pH 6.0, viscosity 120,000 cps.

TABLE 4

Anti-Aging SPF30 CreamF30 Cream

| Components | Quantity |
| --- | --- |
| Water - deionized or distilled | qs. to 100% |
| Hydresia Safflower Oleosomes | 12.0% |
| C12-15 Alkyl Benzoate | 5.0% |
| Avobenzone | 2.5% |
| Octylmethoxycinnamate | 5.0% |
| Dimethicone | 1.0% |
| Arginine | 0.5% |
| Salicylic Acid | 0.5% |
| Glycerin | 2.0% |
| Mixed Tocopherols | 0.05% |
| Superoxide Dismutase | 0.1% |
| Green Tea Extract | 0.2% |
| *Aloe Vera* Extract | 0.5% |
| Allantoin | 0.1% |
| Ammonium Acryloyldimethyl-taurate/ VP Copolymer | 1.0% |
| Phenoxyethanol | 1.0% |
| N-M-A-N-A-K (SEQ ID NO: 1) | 0.0001% |

Procedure: Dissolve the sunscreen filters in the C12-15 alkyl benzoate, mixed tocopherols and dimethicone. Dissolve the aloe vera, green tea, salicylic acid, arginine and glycerin in the water. Mix together with Oleosomes until uniform, this is a cold process. Add the Phenoxyethanol and MNANAK and mix in. Add the thickener slowly and mix until a uniform viscous emulsion results.
Specifications: pH 6.0, viscosity 60,000 cps.

This lotion is a daily use SPF moisturizer product which not only protects the skin from the environmental insult and inflammation caused by sunlight; it helps to restore the skin to a more youthful appearance. The lotion is quick spreading, does not feel oily or greasy, and refreshes the skin as it melds in.

In addition to the examples above, the NF-κB-inhibitor N-M-A-N-A-K (SEQ ID NO: 1) can be formulated into liposomal delivery systems. Liposomes are artificial vesicles formed by amphipathic molecules such as polar lipids, e.g. phosphatidylcholine, ethanol amines and serine, sphingomyelins, cardiolipins, plasmalogens, phosphatidic acids and cerebrosides. Liposomes are formed when amphipathic molecules are allowed to swell in water, or aqueous solutions to form liquid crystals. Liposomes can be either uni-lamellar or bi-lamellar and when made they have particle size between 100 nm and 1 micron.

As mentioned in the examples above, Safflower Oleosomes (Hydresia®, Botaneco Corp, Calgary, Canada) can be used as a natural emulsion to carry the NF-κB-inhibitor, N-M-A-N-A-K (SEQ ID NO: 1), effectively into the skin. Oleosomes are stable vesicles formed by safflower phospholipids and oleosin proteins. They have a particle size of 2 to 4 microns.

VIII. Cosmetic Treatment of the Skin

Ten (10) females, Caucasian, ages 40 to 65, applied the cosmetic cream (TABLE 2) to their faces twice daily over a 1 month period. Photographs were taken (using matched colors) which showed that three things occurred during the testing period:

1) Noticeable reduction of redness;
2) enhancement in skin tone and appearance; and
3) subjects thought their skin looked younger as their lines and wrinkles were minimized and the skin felt softer and smoother to the touch.

While the present invention has been illustrated and described herein in terms of a preferred embodiment and several alternatives, it is to be understood that the techniques described herein can have a multitude of additional uses and applications. Accordingly, the invention should not be limited to just the particular description and various drawing figures contained in this specification that merely illustrate a preferred embodiment and application of the principles of the invention.

What is claimed is:

1. A cosmetic composition, comprising: at least two components, one component being an NF-κB-inhibitor peptide having the sequence N-M-A-N-A-K (SEQ ID NO: 1); and a dermatologically acceptable carrier.

2. The cosmetic composition as in claim 1 wherein the NF-κB-inhibitor peptide is present in an amount effective to inhibit NF-κB activity.

3. The composition as in claim 2 wherein an additional component is a TGF-β mimic.

4. The composition as in claim 3 wherein the TGF-β mimic is a peptide having the sequence A-N-V-A-E-N-A (SEQ ID NO: 2).

5. The composition as in claim 1 wherein the carrier is suitable for topical administration.

6. A method of inhibiting NF-κB activity, comprising: administering to the skin of a patient in need thereof, an effective amount of the cosmetic composition of claim 1.

7. The method as in claim 6 wherein the cosmetic composition of claim 1 is effective in negating mammalian skin maladies and signs of aging skin.

8. The method as in claim 7 wherein said maladies comprise blemishes, lesions, pimples, pre-emergent pimples, blackheads, and/or whiteheads.

9. The method as in claim 7 wherein said signs of aging comprise the need of improvement in firmness or texture, the appearance of lines or wrinkles, or the loss of elasticity.

```
                              SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: NF-kappaB inhibitor

<400> SEQUENCE: 1

Asn Met Ala Asn Ala Lys
1               5

<210> SEQ ID NO 2
<211> LENGTH: 7
<212> TYPE: PRT
<213> ORGANISM: Artificial Sequence
<220> FEATURE:
<223> OTHER INFORMATION: TGF-beta mimic

<400> SEQUENCE: 2

Ala Asn Val Ala Glu Asn Ala
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Arg Ser Arg Lys
1
```

10. A method of treating skin maladies and signs of aging skin of the skin of a mammal in need thereof, comprising applying to said skin the cosmetic composition according to claim 3.

11. The method as in claim 10 wherein the TGF-β mimic reduces inflammation of said skin.

12. The method as in claim 10 wherein the NF-κB-inhibitor peptide has the sequence N-M-A-N-A-K (SEQ ID NO: 1).

13. The method as in claim 10 wherein the TGF-β mimic is a peptide having the sequence A-N-V-A-E-N-A (SEQ ID NO: 2).

14. The method as in claim 10 wherein said maladies comprise blemishes, lesions, pimples, pre-emergent pimples, blackheads, and/or whiteheads.

15. The method as in claim 10 wherein said signs of aging comprise the need of improvement in firmness or texture, the appearance of lines or wrinkles, or the loss of elasticity.

\* \* \* \* \*